US012767658B2

(12) United States Patent
Xiao et al.

(10) Patent No.: US 12,767,658 B2
(45) Date of Patent: Oct. 20, 2026

(54) TETRACYCLIC PYRIMIDINONE COMPOUND, PREPARATION METHOD THEREFOR, AND COMPOSITION AND USE THEREOF

(71) Applicant: NEUSCO BIOTECH LIMITED, Shanghai (CN)

(72) Inventors: Qiong Xiao, Shanghai (CN); Zhenghua Gu, Shanghai (CN); Youhong Hu, Shanghai (CN)

(73) Assignee: NEUSCO BIOTECH LIMITED, Shanghai (CN)

( * ) Notice: Subject to any disclaimer, the term of this patent is extended or adjusted under 35 U.S.C. 154(b) by 1012 days.

(21) Appl. No.: 17/764,862

(22) PCT Filed: Sep. 1, 2020

(86) PCT No.: PCT/CN2020/112802

§ 371 (c)(1),
(2) Date: Mar. 29, 2022

(87) PCT Pub. No.: WO2021/063145

PCT Pub. Date: Apr. 8, 2021

(65) Prior Publication Data

US 2023/0242532 A1 Aug. 3, 2023

(30) Foreign Application Priority Data

Sep. 30, 2019 (CN) ........................ 201910939482.X
Oct. 10, 2019 (CN) ........................ 201910959237.5

(51) Int. Cl.

*C07D 471/22* (2006.01)
*A61P 9/10* (2006.01)
*A61P 25/28* (2006.01)
*A61P 27/06* (2006.01)
*A61P 35/00* (2006.01)
*C07D 487/22* (2006.01)
*C07D 498/22* (2006.01)

(52) U.S. Cl.

CPC .............. *C07D 471/22* (2013.01); *A61P 9/10* (2018.01); *A61P 25/28* (2018.01); *A61P 27/06* (2018.01); *A61P 35/00* (2018.01); *C07D 487/22* (2013.01); *C07D 498/22* (2013.01)

(58) Field of Classification Search

CPC ... C07D 471/22; C07D 487/22; C07D 498/22
See application file for complete search history.

(56) References Cited

U.S. PATENT DOCUMENTS

2017/0204109 A1 7/2017 Wan et al.
2023/0044787 A1* 2/2023 Jin .......................... A61P 25/28

FOREIGN PATENT DOCUMENTS

WO 2013013503 A1 1/2013
WO 2013014185 A1 1/2013
WO 2016011930 A1 1/2016
WO 2016011931 A1 1/2016
WO 2021089032 A1 5/2021

OTHER PUBLICATIONS

Berge et al. (Journal of Pharmaceutical Sciences, 1977, 66(1), 1-19).*

First Office Action issued in corresponding Chinese Application No. 201910959237.5; mailed Aug. 31, 2021; 16 pgs.

Notification of Grant issued in corresponding Chinese Application No. 201910959237.5; mailed Feb. 14, 2022; 4 pgs.

International Search Report and Written Opinion issued in corresponding International Application No. PCT/CN2020/112802; mailed Oct. 28, 2020; 19 pgs.

Stafforini, Diana M.,et al; Human Macrophages Secret Platelet-activating Factor Acetylhydrolase; Journal of Biological Chemistry; vol. 265, No. 17, Jun. 16, 1990; pp. 9682-9687.

Nakajima, Koh-ichi, et al; Activated Mast Cells Release Extracellular Type Platelet-activating Factor Acetylhydrolase That Contributes to Autocrine Inactivation of Platelet-activating Factor; Journal of Biological Chemistry; vol. 272 No. 32, Aug. 8, 1997; pp. 19708-19713.

Caslake, Muriel, et al.; Lipoprotein-associated phospholipase A2, platelet-activating factor acetylhydrolase: a potential new risk factor for coronary artery disease; Atherosclerosis 150; 2000; pp. 413-419.

Quinn, Mark T., et al; Lysophosphatidylcholine: A chemotactic factor for human monocytes and its potential role in atherogenesis; Proc. Natl. Acad. Sci. U S A; vol. 85, pp. 2805-2809, Apr. 1988; pp. 2805-2809.

Bertilsson, Helena, et al.; Changes in Gene Transcription Underlying the Aberrant Citrate and Choline Metabolism in Human Prostate Cancer Samples; Clinical Cancer Research; 18(12); Jun. 15, 2012, pp. 3261-3269.

(Continued)

*Primary Examiner* — Susanna Moore
(74) *Attorney, Agent, or Firm* — HAUPTMAN HAM, LLP

(57) ABSTRACT

Disclosed is a tetracyclic pyrimidinone compound represented by formula (I) or a pharmaceutically acceptable salt thereof. The compound having a structure represented by formula (I) is a new Lp-PLA2 inhibitor usable for treatment of neurodegenerative-related diseases, such as Alzheimer's disease (AD), glaucoma and age-related macular degeneration (AMD), or of cardiovascular diseases including atherosclerosis.

(I)

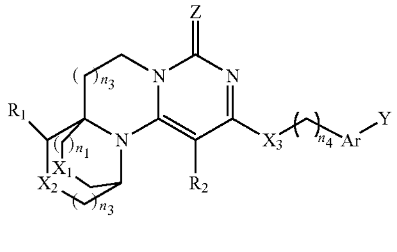

15 Claims, No Drawings

(56) References Cited

OTHER PUBLICATIONS

Echeverria Valentia, et al; Positive modulators of the a7 nicotinic receptor against neuroinflammation and cognitive impairment in Alzheimer's disease; Progress in Neurobiology, 2016, 144, pp. 142-157.
Nagano, Josesph M. G., et al; Selective inhibitors and tailored activity probes for lipoprotein-associated phospholipase A2; Bioorg Med Chem Lett. 2013, 23, pp. 839-843.
Maher-Edwards, Gareth, et al; A 24-week study to evaluate the effect of rilapladib on cognition and cerebrospinal fluid biomarkers of Alzheimer's disease; Alzheimer's & Dementia: Translational Research & Clinical Interventions 1, 2015, pp. 131-140.
Dennis, Edward A., et al; Phospholipase A2 Enzymes: Physical Structure, Biological Function, Disease Implication, Chemical Inhibition, and Therapeutic Intervention; Chemical Reviews; 2011, 111, pp. 6130-6185.
Macphee, Colin H., et al; Lipoprotein-associated phospholipase A2, platelet-activating factor acetylhydrolase, generates two bioactive products during the oxidation of low-density lipoprotein : use of a novel inhibitor; Biochem J. 1999, 338, pp. 479-487.
Shi, Yii, et al; Role of lipoprotein-associated phospholipase A2 in leukocyte activation and inflammatory responses; Atherosclerosis, 2007, 191, 5pp. 54-62.
Wilensky, Robert L., et al; Lipoprotein-associated phospholipase A2 and atherosclerosis; Current Opinion in Lipidology, 2009, 20, pp. 415-420.
Fitzpatrick; Annette L.,et al; Lipoprotein-associated phospholipase A2 and Risk of Dementia in the Cardiovascular Health Study; Atherosclerosis. 2014, 235(2), pp. 384-391.
Staurenghi, Giovanni MD, et al; Darapladib, a Lipoprotein-Associated Phospholipase A2 Inhibitor, in Diabetic Macular Edema; American Academy of Ophthalmology; 2015, 122, pp. 990-996.
Hardy, John, et al; The Amyloid Hypothesis of Alzheimer's Disease: Progress and Problems on the Road to Therapeutics; Science's Compass Review; Jul. 19, 2002, vol. 297, pp. 353-356.
Chiang, Karen, et al.; Emerging Therapeutics for Alzheimer's Disease; Annu. Rev.Pharmacol. Toxicol. ; 2014, 54, pp. 381-405.
Awasthi, Manika, et al; Alzheimer's disease: An overview of amyloid beta dependent pathogenesis and its therapeutic implications along with in silico approaches emphasizing the role of natural products; Journal of the Neurological Sciences; 2016, 361, pp. 256-271.
Kassner, Stefan S., et al.; Novel Systemic Markers for Patients with Alzheimer Disease?—A Pilot Study; Current Alzheimer Research, 2008, 5, pp. 358-366.
Dildar, Konukoglu, MD, et al., Serum Nitrosative Stress Levels Are Increased in Alzheimer Disease but Not in Vascular Dementia; Alzheimer Dis Assoc Disord, vol. 24, Apr.-Jun. 2010; pp. 194-197.
Sinem, F., et al. The Serum Protein and Lipid Oxidation Marker Levels in Alzheimer's Disease and Effects of Cholinesterase Inhibitors and Antipsychotic Drugs Therapy; Current Alzheimer Research, 2010, 7, pp. 463-469.
Colangelo, Vittorio, et al; Gene Expression Profiling of 12633 Genes in Alzheimer Hippocampal CA1: Transcription and Neurotrophic Factor Down-Regulationand Up-Regulation of Apoptotic and Pro-Inflammatory Signaling; Journal of Neuroscience Research, 2002, 70, pp. 462-473.
Wyss-Coray, Tony; Inflammation in Alzheimer disease: driving force, bystander or beneficial response?; Nature Medicine, vol. 12; No. 9; Sep. 2006; pp. 1005-1015.
Bushchini, Elisa, et al; Age related macular degeneration and drusen: Neuroinflammation in the retina; Progress in Neurobiology, 2011, 95, pp. 14-25.
Tew, David G., et al; Mechanism of Inhibition of LDL Phospholipase A2 by Monocyclic-B-lactams. Burst Kinetics and the Effect of Stereochemistry; Biochemistry, 1998, 37, pp. 10087-10093.
Jeong, Tae-Sook, et al, (E)-Phenyl- and -heteroaryl-substituted O-benzoyl- (oracyl)oximes as lipoprotein-associated phospholipase A2 inhibitors; Bioorganic & Medicinal Chemistry Letters, 2005, 15, pp. 1525-1527.
Jeong, Hyung Jae, et al; Potent inhibitors of lipoprotein-associated phospholipase A2: Benzaldehyde O-heterocycle-4-carbonyloxime, Bioorganic & Medicinal Chemistry Letters, 2006, 16, pp. 5576-5579.
LIn, Emme C.K., et al; Amides of xanthurenic acid as zinc-dependent inhibitors of Lp-PLA2; Bioorganic & Medicinal Chemistry Letters, 2012, 22, pp. 868-871.
Hu, Yi, et al.; Amides of 4-hydroxy-8-methanesulfonylamino-quinoline-2-carboxylic acid as zinc-dependent inhibitors of Lp-PLA2; Bioorganic & Medicinal Chemistry Letters 2013, 23, pp. 1553-1556.
Magrioti, Victoria, et al; Phospholipase A2 inhibitors for the treatment of inflammatory diseases: a patent review (2010-present); Expert Opin Ther Pat. 2013; 23; pp. 333-344.
Annette L. Fitzpatrick, et al., "Lipoprotein-associated phospholipase A2 and Risk of Dementia in the Cardiovascular Health Study", Atherosclerosis, Apr. 28, 2014, doi: 10.1016/j.atherosclerosis.2014.04.032.; 31 pgs.
Chen et al., "Discovery of Potent and Orally Active Lipoprotein-Associated Phospholipase A2 (Lp-PLA2) Inhibitors as a Potential Therapy for Diabetic Macular Edema", Journal of Medicinal Chemistry, published Feb. 29, 2016; 14 pgs.
Elisa Buschini et al., "Age related macular degeneration and drusen: Neuroinflammation in the retina", Progress in Neurobiology 95 (2011), Jun. 28, 2011, 14-25; 12 pgs.
Examination Report in Corresponding Canadian Application No. 3,152,457, dated Jun. 17, 2025; 4 pgs.
Examination Report in Corresponding European Application No. 20 872 471.6, dated Aug. 25, 2025; 5 pgs.
Examination Report No. 1 in Corresponding Australian Application No. 2020358539, dated Jun. 11, 2025; 3 pgs.
Extended Search Report in Corresponding European Application No. 20 872 471.6, dated Sep. 4, 2023; 9 pgs.
First Office Action in Corresponding Russian Application No. 2022111339/04, dated Nov. 30, 2022; 18 pgs.
Gareth Maher-Edwards et al., "A 24-week study to evaluate the effect of rilapladib on cognition and cerebrospinal fluid biomarkers of Alzheimer's disease", Alzheimer's & Dementia: Translational Research & Clinical Interventions 1 (2015) 131-140; 10 pgs.
Giovanni Staurenghi et al., "Darapladib, a Lipoprotein-Associated Phospholipase A2 Inhibitor, in Diabetic Macular Edema—A 3-Month Placebo-Controlled Study," American Academy of Ophthalmology, Dec. 2014; 7 pgs.
Helena Bertilsson et al., "Changes in Gene Transcription Underlying the Aberrant Citrate and Choline Metabolism in Human Prostate Cancer Samples", Clinical Cancer Research; 18(12) Jun. 15, 2012; 9 pgs.
Notice of Preliminary Rejection in Corresponding Korean Application No. 10-2022-7011711, dated Mar. 21, 2024; 9 pgs.
Notice of Reasons for Refusal in Corresponding Japanese Application No. 2022-520501, mailed Mar. 7, 2023; 6 pgs.
Notice of Reasons for Refusal No. 2 in Corresponding Japanese Application No. 2022-520501, mailed Sep. 12, 2023; 5 pgs.
Notice of Reasons for Refusal No. 3 in Corresponding Japanese Application No. 2022-520501, mailed Jan. 9, 2024; 5 pgs.
Notice of Reasons for Refusal No. 4 in Corresponding Japanese Application No. 2022-520501, mailed May 28, 2024; 4 pgs.
Request for the Submission of an Opinion in Corresponding Korean Application No. 10-2022-7011711, dated Jan. 16, 2025; 9 pgs.
Search Report and Written Opinion in Corresponding Singapore Application No. 11202203267W, dated Jun. 26, 2023; 7 pgs.
Second Office Action in Corresponding Russian Application No. 2022111339/04, dated May 30, 2023; 7 pgs.

* cited by examiner

TETRACYCLIC PYRIMIDINONE COMPOUND, PREPARATION METHOD THEREFOR, AND COMPOSITION AND USE THEREOF

RELATED APPLICATIONS

The present application is a U.S. National Phase of International Application Number PCT/CN2020/112802, filed Sep. 1, 2020, and claims priority to Chinese Application Numbers CN 201910939482.X filed Sep. 30, 2019, and CN 201910959237.5 filed Oct. 10, 2019.

TECHNICAL FIELD

The present disclosure belongs to the field of medicine, and specifically relates to a tetracyclic pyrimidinone compound, a preparation method therefor, and a composition thereof, and use thereof in medicine.

BACKGROUND

Lipoprotein-associated phospholipase A2 (Lp-PLA2) is a member of the phospholipase A2 superfamily (Dennis E A, Cao J, Hsu Y H, Magrioti V, Kokotos G. Chem Rev. 2011, 111, 6130-6185). It is mainly secreted by monocytes, macrophages, T lymphocytes, and chief cells (Stafforini D M, Elstad M R, McIntyre T M, Zimmerman G A, Prescott S M. J Biol Chem. 1990, 265:9682-9687; Nakajima K, Murakami M, Yanoshita R, Samejima Y, Karasawa K, Setaka M, Nojima S Kudo I. J Biol Chem. 1997, 272, 19708-19713). Phosphatidylcholine sn-2 esters are produced during oxidation of low-density lipoprotein (LDL), and Lp-PLA2 is responsible for hydrolysis of oxidatively modified phosphatidylcholine sn-2 esters, and then producing oxidized fatty acids and lysophosphatidylcholine (LysoPC) (Caslake M J, Packard C J, Suckling K E, Holmes S D, Chamberlain P, Macphee C H. Atherosclerosis. 2000, 150, 413-419; MacPhee C H, Moores K E, Boyd H F, Dhanak D, Ife R J, Leach C A, Leake D S, Milliner K J, Patterson R A, Suckling K E, Tew D G, Hickey D M. Biochem J. 1999, 338, 479-487). Both oxidized fatty acids and LysoPC play roles in activating macrophages, increasing oxidative stress, affecting T lymphocyte function, and inducing inflammatory responses (Quinn M T, Parthasarathy S, Steinberg D. Proc Natl Acad Sci USA. 1988, 85, 2805-2809). LysoPC has been reported to induce the release of multiple cytotoxic inflammatory cytokines (Shi, et al, Atherosclerosis, 2007, 191, 54-62). In addition, LysoPC is also involved in leukocyte activation, induction of apoptosis, and mediation of endothelial dysfunction (Wilensky et al, Current Opinion in Lipidology, 2009, 20, 415-420).

It has been reported that the Lp-PLA2 level of plasma is associated with cardiovascular diseases (Fitzpatrick A L, Irizarry M C, Cushman M, Jenny N S, Chi G C, Koro C. *Atherosclerosis.* 2014, 235, 384-391), diabetic macular edema (DME) (Staurenghi G, Ye L, Magee M H, Danis R P, Wurzelmann J, Adamson P, McLaughlin M M, Darapladib DMESG. *Ophthalmology.* 2015, 122, 990-996), and prostate cancer (Bertilsson H, Tessem M B, Flatberg A, Viset T, Gribbestad I, Angelsen A, Halgunset J. *Clin Cancer Res.* 2012, 18, 3261-3269).

Alzheimer's disease (AD) is a chronic neurodegenerative disease that causes cognitive decline, mood swing, irreversible memory loss, disorientation, language impairment, and loss of self-protection (Hardy J, et al. Science 2002, 297, 353-356). Alzheimer's disease typically begins slowly and gets progressively worse over time, which is responsible for 60 to 70 percent of dementia cases and affects about 6 percent of the population over the age of 65. AD patients will gradually withdraw from family and society, become more and more dependent on help, and eventually progress to death. AD is one of the most costly diseases in developed countries, so as in other countries. Especially as aging becomes an important social issue, the costs will increase dramatically. There is no doubt that AD is a complex disease involving multiple factors. Although the pathogenesis of AD has not been fully elucidated, it is clear that several factors are involved in the development and progression of the disease, including aggregated tau proteins and Aβ peptides, oxidative stress and neuroinflammation (Echeverria V, Yarkov A, Aliev G. *Prog Neurobiol.* 2016, 144, 142-157). Current AD drug discovery focuses mainly on the targets of Aβ amyloidosis and tau (Chiang K, Koo E H. *Annu Rev Pharmacol Toxicol.* 2014, 54, 381-405; Awasthi M, Singh S, Pandey V P, Dwivedi U N. *J Neurol Sci.* 2016, 361, 256-271). However, despite reliable preclinical data, results from late-stage clinical trials have so far failed to demonstrate the clinical efficacy. These disappointing results suggest that other neuropathological mechanisms, such as oxidative stress and neuroinflammation, may have to be explored for AD treatment.

Elevated levels of Lp-PLA2 in plasma increase the risk of dementia, including AD (Van Oijen, et al. Annals of Neurology, 2006, 59,139). Vascular dementia and mixed dementia as well as high oxidative LDL levels have been found in AD patients (Maher-Edwards G, De'Ath J, Barnett C, Lavrov A, Lockhart A, Alzheimer's & Dementia: Translational Research & Clinical Interventions. 2015, 1, 131-140; Kassner et al. Current Alzheimer Research, 2008, 5, 358-366; Dildar, et al., Alzheimer Dis Assoc Disord, 24, April-June (2010); Sinem, et al. Current Alzheimer Research, 2010, 7, 463-469). Neuroinflammation and a plurality of up-regulated inflammatory cytokines have also been found in AD patients (Colangelo, et al., Journal of Neuroscience Research, 2002, 70, 462-473; Wyss-Coray, Nature Medicine, 2006, 12, Sept.).

In view of all of these findings, Lp-PLA2 is a potential target for the treatment of AD, which is further confirmed by the clinical results of Lp-PLA2 inhibitor Rilapladib in AD patients (Maher-Edwards G, De'Ath J, Barnett C, Lavrov A, Lockhart A, *Alzheimer's & Dementia: Translational Research & Clinical Interventions.* 2015, 1, 131-140).

Glaucoma and age-related macular degeneration (AMD) are retinal neurodegenerative diseases. Buschini, et al. have reported that inflammation, including TNF-α signaling, may play an important role in the pathogeneses of glaucoma and AMD (Buschini et al, Progress in Neurobiology, 2011, 95, 14-25; Tezel, Progress in Brain Research, vol. 173, ISSN0079-6123, Chapter 28). In addition, Shi, et al. have demonstrated that the Lp-PLA2 inhibitor can block the release of inflammatory cytokines (Shi, et al, Atherosclerosis, 2007, 191, 54-62). Inhibition of Lp-PLA2 is a potential therapy for glaucoma and AMD.

Many Lp-PLA2 inhibitors have been reported, including β-lactams (Tew D G, Boyd H F, Ashman S, Theobald C, Leach C A. Biochemistry. 1998, 37, 10087-10093), oximes (Jeong T S, Kim M J, Yu H, Kim H S, Choi J K, Kim S S, Lee W S. Bioorg Med Chem Lett. 2005, 15, 1525-1527; Jeong H J, Park Y D, Park H Y, Jeong I Y, Jeong T S, Lee W S. Bioorg Med Chem Lett. 2006, 16, 5576-5579), amides of xanthuric acids (Lin E C, Hu Y, Amantea C M, Pham L M, Cajica J, Okerberg E, Brown H E, Fraser A, Du L, Kohno Y, Ishiyama J, Kozarich J W, Shreder K R. Bioorg Med Chem Lett. 2012, 22, 868-871; Hu Y, Lin E C, Pham L M, Cajica J, Amantea C M, Okerberg E, Brown H E, Fraser A, Du L, Kohno Y, Ishiyama J, Kozarich J W, Shreder K R. Bioorg Med Chem Lett. 2013, 23, 1553-1556), and urethane (Nagano J M, Hsu K L, Whitby L R, Niphakis M J, Speers A E, Brown S J, Spicer T, Fernandez-Vega V, Ferguson J, Hodder P, Srinivasan P, Gonzalez T D, Rosen H, Bahnson B J, Cravatt B F. Bioorg Med Chem Lett. 2013, 23, 839-843).

The Lp-PLA2 inhibitor Darapladib has been reported as a potential therapy against atherosclerosis and DME (Magrioti V, Kokotos G. Expert Opin Ther Pat. 2013; 23:333-344).

SUMMARY

The present inventors have found that Lp-PLA2 inhibitors have a significant role in treatment of neurodegenerative-related diseases such as Alzheimer's disease (AD), glaucoma and age-related macular degeneration (AMD), or cardiovascular diseases including atherosclerosis. To this end, the present inventors are dedicated to developing a brand new Lp-PLA2 inhibitor, i.e., tetracyclic pyrimidinone compound.

The tetracyclic pyrimidinone compound is a compound having a structure represented by formula (I), (I)

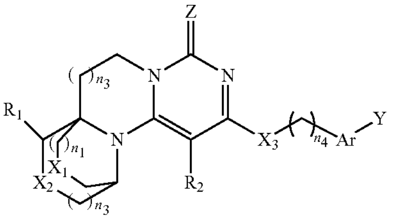

or a pharmaceutically acceptable salt thereof, wherein:

$n_1$, $n_2$, $n_3$, and $n_4$ are each independently 0, 1, or 2;

$R^1$ and $R^2$ are each independently selected from: —H, hydroxyl, cyano, halogen, alkyl, deuteroalkyl, hydroxyalkyl, haloalkyl, cycloalkyl, and alkoxyl;

$X_1$, $X_2$, and $X_3$ are each independently selected from: alkylene, —O—, —S—, or —NR'—;

R' is selected from: —H, alkyl, deuteroalkyl, or cycloalkyl;

Ar is arylene or heteroarylene; and hydrogen atoms in the arylene or heteroarylene are optionally substituted by one or more substituents that are each independently selected from: halogen, alkyl, haloalkyl, alkoxyl, haloalkoxyl, deuteroalkyl, deuteroalkoxyl, hydroxyl, hydroxyalkyl, cyano, amino, monoalkyl- or dialkyl-substituted amino, nitro, carboxyl, aldehyde, cycloalkyl, heterocyclyl, aryl, or heteroaryl;

Y is —H, halogen, alkyl, haloalkyl, haloalkoxyl, cycloalkyl, alkoxyl, deuteroalkyl, deuteroalkoxyl, —OAr', —SAr', —NH—Ar', —NMe—Ar', —NR'', or —R'''—Ar';

Ar' is selected from aryl or heteroaryl; and hydrogen atoms in the aryl or heteroaryl are optionally substituted by one or more substituents that are each independently selected from: halogen, alkyl, haloalkyl, alkoxyl, hydroxyl, hydroxyalkyl, haloalkoxyl, deuteroalkyl, deuteroalkoxyl, cyano, amino, nitro, carboxyl, aldehyde, cycloalkyl, heterocyclyl, aryl, or heteroaryl;

R'' is alkyl;

R''' is alkylene; and

Z is O or S;

optionally, wherein:

$n_1$, $n_2$, $n_3$, and $n_4$ are each independently 0, 1, or 2;

$R^1$ and $R^2$ are each independently selected from: —H, hydroxyl, cyano, halogen, alkyl, deuteroalkyl, hydroxyalkyl, haloalkyl, cycloalkyl, and alkoxyl;

$X_1$, $X_2$, and $X_3$ are each independently selected from: alkylene, —O—, —S—, or —NR'—, R' is selected from: —H, alkyl, deuteroalkyl, or cycloalkyl;

Ar is arylene or heteroarylene; and hydrogen atoms in the arylene or heteroarylene are optionally substituted by one or more substituents that are each independently selected from: halogen, alkyl, haloalkyl, alkoxyl, haloalkoxyl, hydroxyl, hydroxyalkyl, cyano, amino, monoalkyl- or dialkyl-substituted amino, nitro, carboxyl, aldehyde, cycloalkyl, heterocyclyl, aryl, or heteroaryl;

Y is —H, halogen, alkyl, haloalkyl, haloalkoxyl, cycloalkyl, alkoxyl, —OAr', —SAr', —NH—Ar', —NMe—Ar', —NR'', or —R'''—Ar';

Ar' is selected from aryl or heteroaryl; and hydrogen atoms in the aryl or heteroaryl are optionally substituted by one or more substituents that are each independently selected from: halogen, alkyl, haloalkyl, alkoxyl, hydroxyl, hydroxyalkyl, haloalkoxyl, cyano, amino, nitro, carboxyl, aldehyde, cycloalkyl, heterocyclyl, aryl, or heteroaryl;

R'' is alkyl;

R''' is alkylene; and

Z is O or S.

Optionally, halogen atoms in the "halogen", "haloalkyl", and "haloalkoxyl" are each independently selected from F, Cl, Br, or I;

optionally, alkyls in the "alkyl", "deuteroalkyl", "deuteroalkoxyl", "hydroxyalkyl", "haloalkyl", "haloalkoxyl", "alkoxyl", "monoalkyl- or dialkyl-substituted amino" are each independently $C_1$-$C_{10}$ linear or branched alkyl; optionally, $C_1$-$C_7$ linear or branched alkyl; optionally, $C_1$-$C_4$ linear or branched alkyl; and optionally, selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl;

optionally, the "alkylenes" are each independently $C_1$-$C_{10}$ linear or branched alkylene; optionally, $C_1$-$C_7$ linear or branched alkylene; optionally, $C_1$-$C_5$ linear or branched alkylene; optionally, selected from methylene, ethylene, n-propylidene, isopropylidene, n-butylidene, isobutylidene, tert-butylidene, sec-butylidene, n-pentylidene, 1-methylbutylidene, 2-methylbutylidene, 3-methylbutylidene, isopentylidene, 1-ethylpropylidene, neopentylidene, n-hexylidene, 1-methylpentylidene, 2-methylpentylidene, 3-methylpentylidene, isohexylidene, 1,1-dimethylbutylidene, 2,2-dimethylbutylidene, 3,3-dimethylbutylidene, 1,2-dimethylbutylidene, 1,3-dimethylbutylidene, 2,3-dimethylbutylidene, 2-ethylbutylidene, n-heptylidene, 2-methylhexylidene, 3-methylhexylidene, 2,2-dimethylpentylidene, 3,3-dimethylpentylidene, 2,3-dimethylpentylidene, 2,4-dimethylpentylidene, 3-ethylpentylidene, or 2,2,3-trimethylbutylidene;

optionally, the "cycloalkyl" is $C_3$-$C_{10}$ monocyclic or bicyclic cycloalkyl, optionally $C_3$-$C_7$ monocyclic cycloalkyl, and optionally cyclopropyl, cyclobutyl, cyclopentyl, cyclohexyl, or cycloheptyl;

optionally, the "heterocyclyl" is 3- to 10-membered non-aromatic heterocyclic ring containing 1, 2, or 3 heteroatoms selected from N, O, and S on the ring, optionally, the heterocyclic ring is a 3- to 10-membered non-aromatic ring containing 1 or 2 heteroatoms selected from N and O on the ring; optionally, the heterocyclic ring is a 3- to 6-membered non-aromatic ring containing 1 or 2 heteroatoms selected from N and O on the ring; optionally, the heterocyclic ring is a 3- to 10-membered non-aromatic ring containing 1 or 2 heteroatoms selected from N and S on the ring; and optionally, the heterocyclic ring is a 3- to 6-membered non-aromatic ring containing 1 or 2 heteroatoms selected from N and S on the ring;

optionally, the "aryl" is 6- to 10-membered aryl, optionally phenyl or naphthyl, and optionally phenyl, 1-naphthyl, or 2-naphthyl;

optionally, the "arylene" is 6- to 10-membered arylene, and optionally phenylene or naphthylene;

optionally, the "heteroaryl" is a 5- to 10-membered heteroaromatic ring containing 1 to 3 heteroatoms selected from N, O, and S on the ring, and optionally a 5- to 10-membered heteroaromatic ring containing 1 to 2 heteroatoms selected from N, O, and S on the ring; optionally, the heteroaromatic ring is selected from a pyridine ring, a pyrrole ring, a pyrimidine ring, a pyrazine ring, a pyridazine ring, a thiophene ring, and a furan ring; optionally, the heteroaryl is selected from pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, pyrazin-3-yl, indolyl, isoindolyl, indazolyl, indolizinyl, purinyl, quinolizinyl, quinolinyl, isoquinolinyl, cinolinyl, phthalazinyl, naphthyridinyl, quinazolinyl, quinoxalinyl, thieno[2,3-b]furyl, furo[3,2-b]-pyranyl, pyrido[2,3-d]oxazinyl, pyrazolo[4,3-d]oxazolyl, imidazo[4,5-d]thiazolyl, pyrazino[2,3-d]pyridazinyl, imidazo[2,1-b]thiazolyl, imidazo[1,2-b][1,2,4]triazinyl, benzothienyl, benzoxazolyl, benzimidazolyl, benzothiazolyl, benzoxepinyl, benzoxazinyl, benzofuranyl, benzotriazolyl, pyrrolo[2,3-b]pyridyl, pyrrolo[3,2-c]pyridyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridyl, pyrazolo[3,4-d]pyridyl, pyrazolo[3,4-b]pyridyl, imidazo[1,2-a]pyridyl, pyrazolo[1,5-a]pyridyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazolo[2,3-b]pyrazinyl, and pyrimido[4,5-d]pyrimidinyl, and optionally pyridin-2-yl, pyridin-3-yl, pyridin-4-yl, pyrimidin-2-yl, pyrimidin-4-yl, or pyrimidin-5-yl;

optionally, the "heteroarylene" is a 5- to 10-membered heteroarylene ring containing 1 to 3 heteroatoms selected from N, O, and S on the ring, and optionally a 5- to 10-membered heteroarylene ring containing 1 to 2 heteroatoms selected from N, O, and S on the ring; and optionally, the heteroarylene ring is selected from a pyridylidene ring, a pyrrylidene ring, a pyrimidylidene ring, a pyrazinylidene ring, a pyridazinylidene ring, a thienylidene ring, a furylidene ring.

optionally, $n_1$, $n_2$, $n_3$, and $n_4$ are each independently 0, 1, or 2; optionally, $n_1$ is 0, optionally, $n_2$ is 0 or 1, optionally, $n_3$ is 0, optionally, $n_4$ is 1;

optionally, $R^1$ and $R^2$ are each independently selected from: —H, F, Cl, Br, hydroxyl, cyano, $C_1$-$C_7$ alkyl (methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), $C_1$-$C_3$ deuteroalkyl (—$CD_3$, —$C_2D_5$, —$C_3D_7$), cyclopropanyl, cyclobutanyl, and cyclopentyl; optionally, $R^1$ is —H, optionally, $R^2$ is —H;

optionally, $X_1$, $X_2$, and $X_3$ are each independently selected from: $C_1$-$C_7$ alkylene (optionally, —$CH_2$—, ethylene, n-propylidene, isopropylidene, n-butylidene, or isobutylidene), —O—, —S—, or —NR'—; optionally, $X_1$ is —$CH_2$—; optionally, $X_2$ is selected from —$CH_2$— or —O—; optionally, $X_3$ is —O—;

optionally, R' is selected from-H, $C_1$-$C_7$ alkyl (methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), deuteroalkyl (optionally —$CD_3$, —$C_2D_5$, —$C_3D_7$), or $C_3$-$C_6$ cycloalkyl (cyclopropanyl, cyclobutanyl, cyclopentyl, or cyclohexyl);

optionally, Ar is phenylene or pyridyl, and a hydrogen atom in the phenylene or pyridyl is optionally substituted by 1, 2, or 3 substituents that are each independently selected from: F, Cl, Br, I, —CN, —Me, —$C_2H_5$, cyclopropyl, —$CD_3$, —OMe, or —OCF3; optionally, Ar is phenylene, and a hydrogen atom in the phenylene is optionally substituted by 2 substituents that are F;

optionally, Y is —H, —F, —Cl, —Br, methyl, ethyl, n-propyl, isoproyl, —$CD_3$, —$CF_3$, —$CH_2CF_3$, —$OCF_3$, —$OCHF_2$, cyclopropyl, -cyclobutyl, -cyclopentyl, —$OCH_3$, —$OC_2H_5$, —$OC_3H_7$, or —OAr'; optionally, Y is —H or —OAr';

optionally, Ar' is selected from phenyl, pyridyl, pyrimidinyl, or quinolinyl, and hydrogen atoms in the phenyl, pyridyl, pyrimidinyl or quinolinyl ring are each independently optionally substituted with 1, 2 or 3 substituents that are each independently selected from: F, Cl, Br, —CN, $C_1$-$C_7$ alkyl (optionally selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), —$CD_3$, $C_1$-$C_6$haloalkyl, —$OCH_3$, —$OC_2H_7$, —$OC_3H_7$, $C_1$-$C_6$ haloalkoxyl, or $C_3$-$C_6$cycloalkyl (optionally cyclopropanyl, cyclobutanyl, cyclopentyl, or cyclohexyl); optionally, Ar' is selected from phenyl, pyridin-3-yl, or pyridin-4-yl, or pyrimidin-5-yl, optionally, the Ar' is substituted by 1 or 2 substituents that are selected from Cl, —$CH_3$, —$CF_3$, or —$OCF_3$; and optionally, Z is O.

Optionally, the compound of formula (I), or the pharmaceutically acceptable salt thereof, wherein the compound of formula (I) is selected from the following compounds:

1

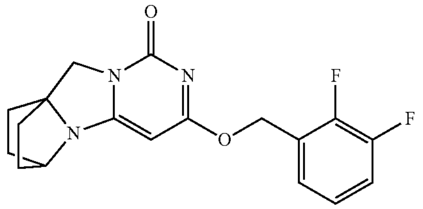

2

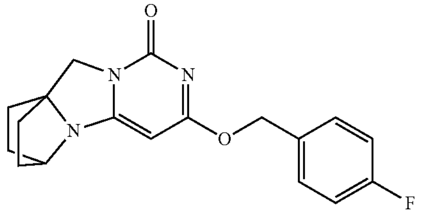

3

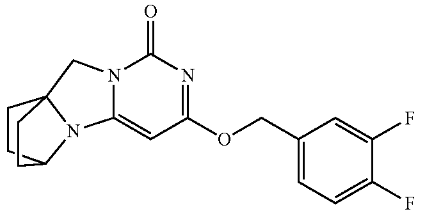

4

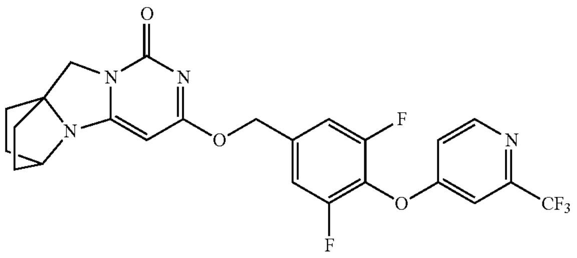

5

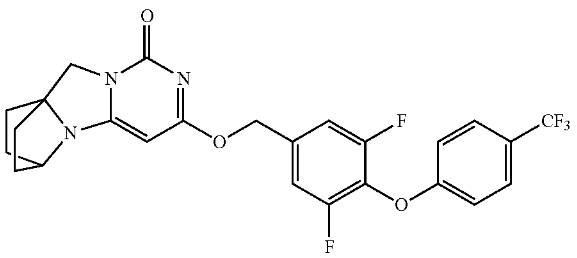

-continued

6

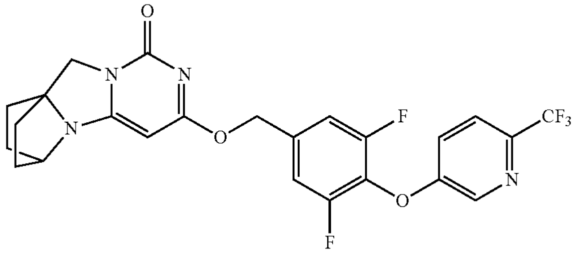

7

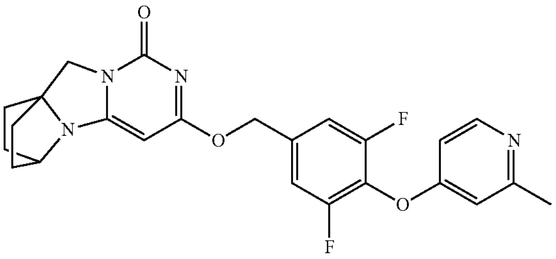

8

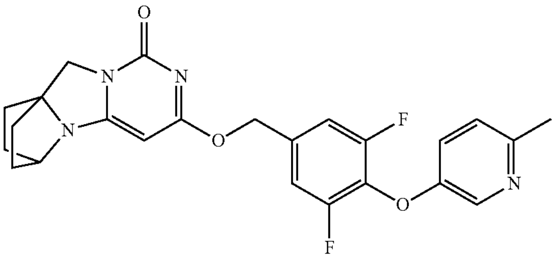

9

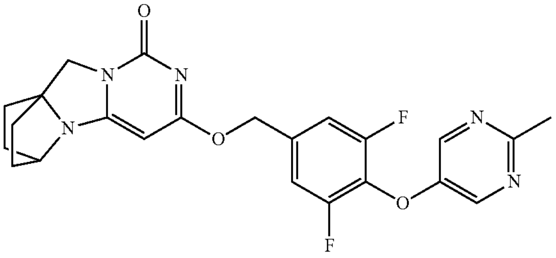

10

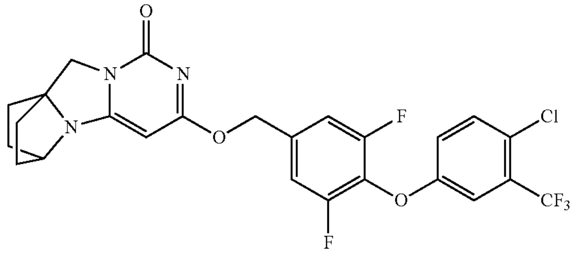

-continued

11

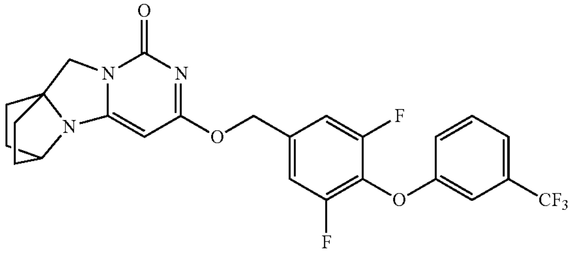

12

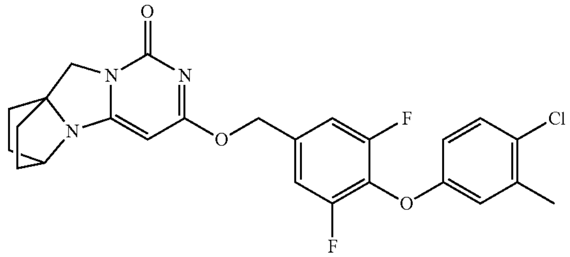

13

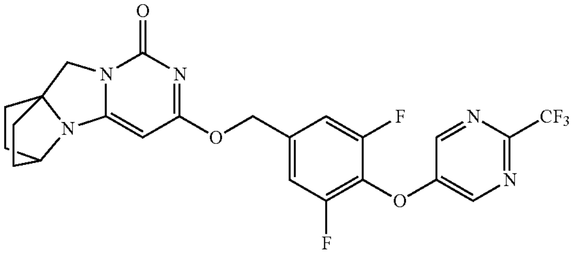

14

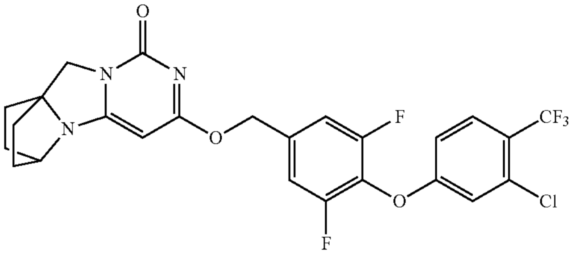

15

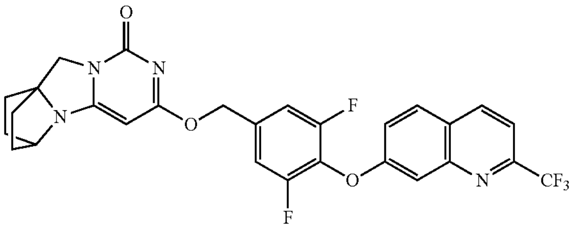

-continued

16

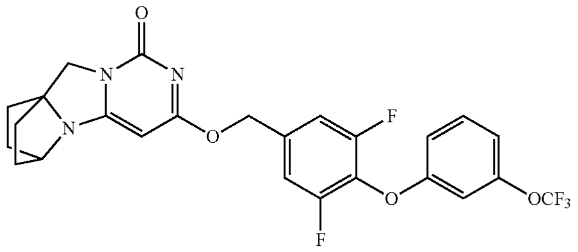

17

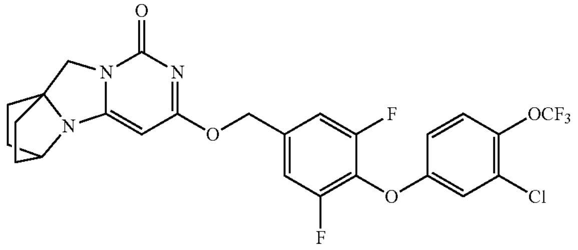

18

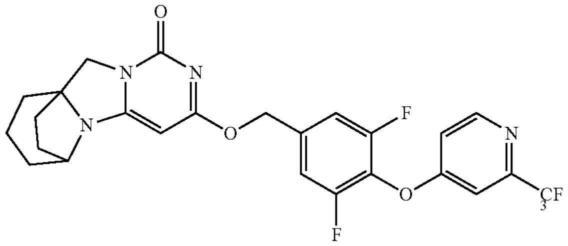

19

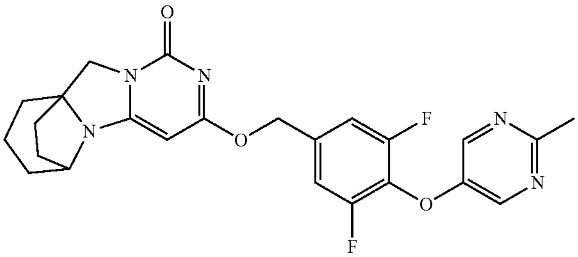

20

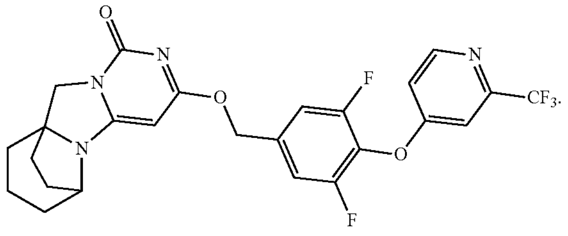

Optionally, the compound of formula (I), or the pharmaceutically acceptable salt thereof, wherein the pharmaceutically acceptable salt includes an anionic salt and a cationic salt of the compound of formula (I);

optionally, the pharmaceutically acceptable salt includes an alkali metal salt, an alkaline earth metal salt, and an ammonium salt of the compound of formula (I); optionally, the alkali metal includes sodium, potassium, lithium, and cesium, and the alkaline earth metal includes magnesium, calcium, and strontium;

optionally, the pharmaceutically acceptable salt includes a salt formed by the compound of formula (I) and an organic base;

optionally, the organic base includes trialkylamine, pyridine, quinoline, piperidine, imidazole, picoline, dimethylaminopyridine, dimethylaniline, N-alkylmorpholine, 1,5-diazabicyclo[4.3.0]nonene-5, 1,8-diazabicyclo[5.4.0]undecene-7, and 1,4-diazabicyclo [2.2.2]octane; optionally, the trialkylamine includes trimethylamine, triethylamine, and N-ethyldiisopropylamine; and optionally, the N-alkylmorpholine includes N-methylmorpholine;

optionally, the pharmaceutically acceptable salt includes a salt formed by the compound of formula (I) and an acid; and optionally, the acid includes an inorganic acid and an organic acid; optionally, the inorganic acid includes hydrochloric acid, hydrobromic acid, hydroiodic acid, sulfuric acid, nitric acid, phosphoric acid, carbonic acid; optionally, the organic acid includes formic acid, acetic acid, propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid, glutamic acid, and pamoic acid.

In another aspect, provided is a method for preparing a compound of formula (I), or a pharmaceutically acceptable salt thereof, the method comprising the following reaction route:

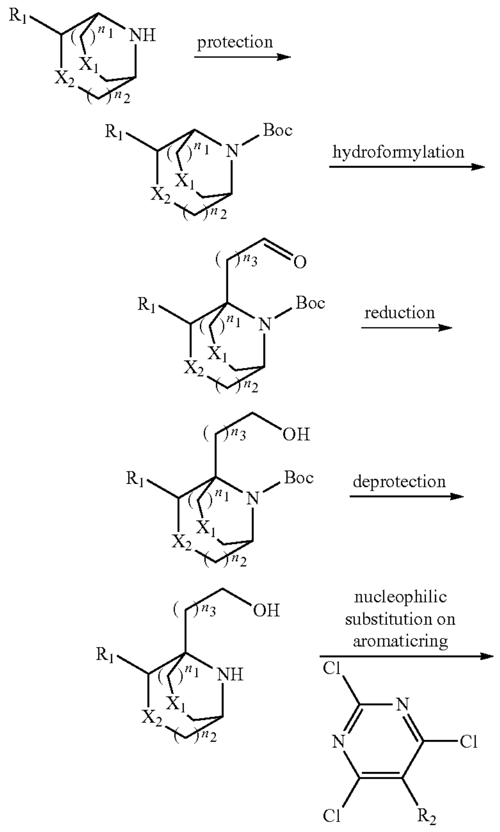

-continued

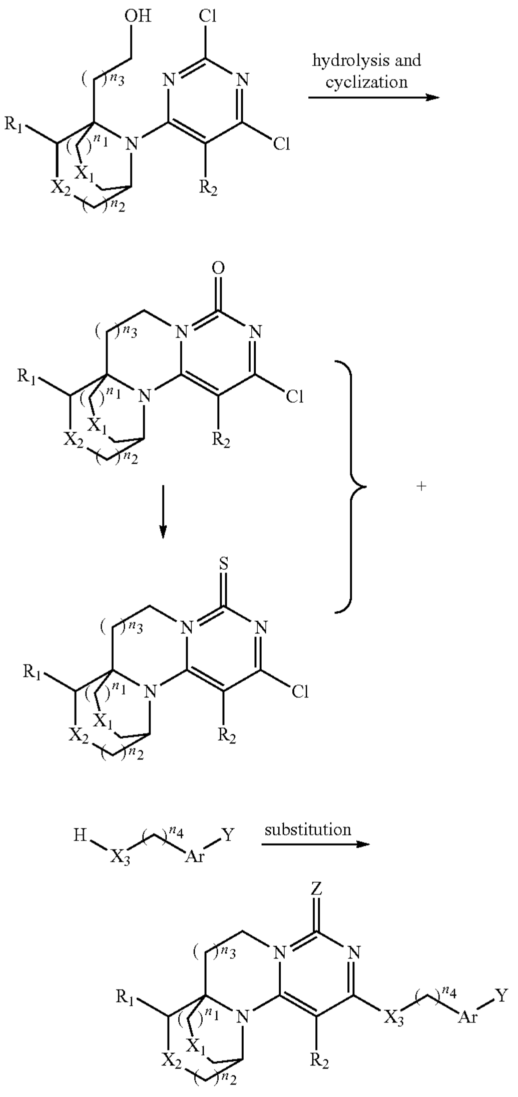

in respective formulas, $n_1$, $n_2$, $n_3$, $R^1$, $R^2$, $X_1$, $X_2$, $X_3$, Z, Ar, and Y are as defined above;

optionally, when $X_2$ is —O— and $n_3$ is 0, the following synthetic route is further adopted:

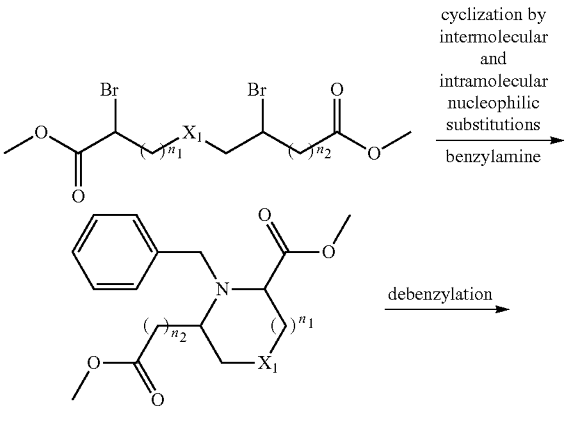

-continued

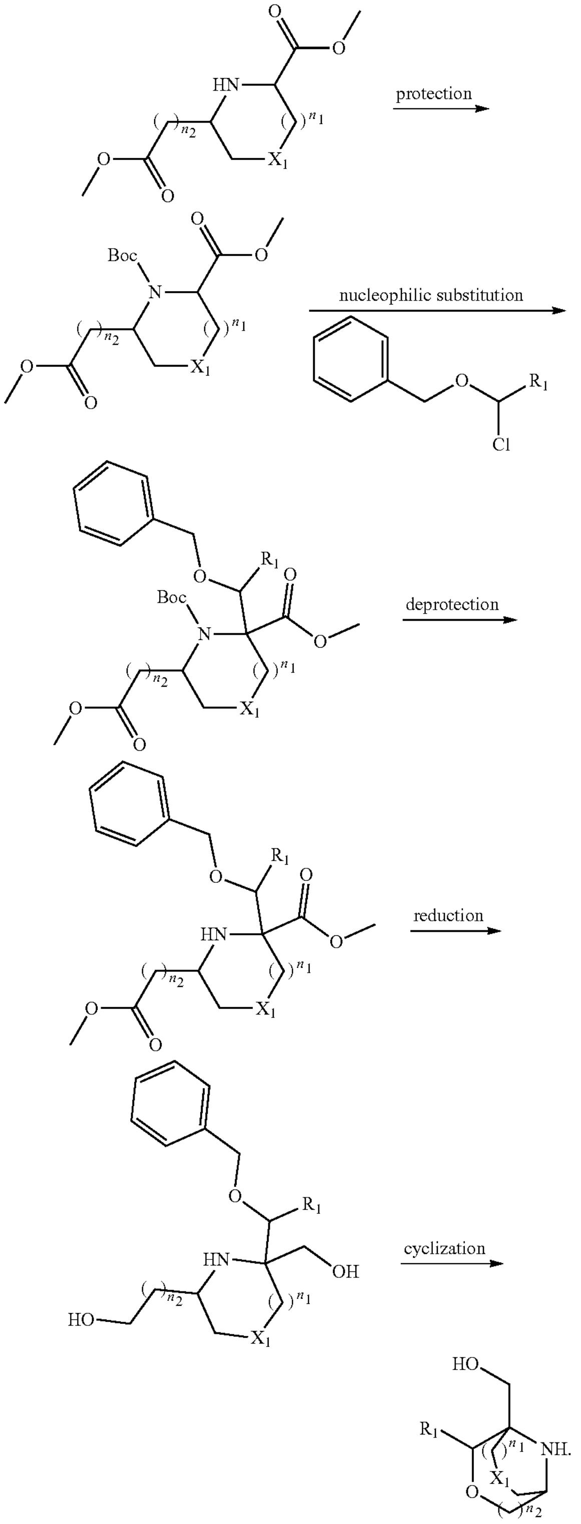

The specific reaction conditions for each of the above-mentioned reactions are not particularly limited, and existing conventional reaction conditions or steps can be used.

In another aspect, provided is a pharmaceutical composition, comprising a therapeutically effective dose of one or more of the above-mentioned compound of formula (I), or pharmaceutically acceptable salt thereof, and optionally a pharmaceutically acceptable carrier.

optionally, a dosage form of the pharmaceutical composition includes an oral preparation, a rectally administered preparation, and a parenteral administered preparation;

optionally, the oral preparation includes a solid preparation and a liquid preparation;

optionally, the solid preparation includes tablets, powders, granules, and capsules;

optionally, the liquid preparation includes aqueous or oily suspensions, and syrups; and optionally, the parenteral administered preparation includes solutions for injection, and aqueous or oily suspensions.

In another aspect, provided is use of a compound of formula (I) or a pharmaceutically acceptable salt thereof as described above, or a pharmaceutical composition as described above in the preparation of an Lp-PLA2 inhibitor.

In another aspect, provided is use of a compound of formula (I) or a pharmaceutically acceptable salt thereof as described above, or a pharmaceutical composition as described above in the preparation of a medicament for treating a neurodegenerative-related disease; and optionally, the neurodegenerative-related disease includes Alzheimer's disease (AD), glaucoma, and age-related macular degeneration (AMD).

In another aspect, provided is use of a compound of formula (I) or a pharmaceutically acceptable salt thereof as described above, or a pharmaceutical composition as described above in the preparation of a medicament for treating cardiovascular disease, diabetic macular edema (DME), or prostatic disease; and optionally, the cardiovascular disease includes atherosclerosis.

Beneficial Effects

The compound of formula (I) is a tetracyclic pyrimidinone compound, which is a brand new Lp-PLA2 inhibitor. It is useful for treating neurodegenerative-related diseases, such as Alzheimer's disease (AD), glaucoma and age-related macular degeneration (AMD), or cardiovascular diseases including atherosclerosis.

DETAILED DESCRIPTION

The present disclosure will be further explained with reference to the following examples. It should be appreciated that the examples described herein are merely intended to exemplarily illustrate the present disclosure, and not limit the scope of the present disclosure in any way.

The starting materials of the present disclosure can be synthesized by or according to the methods known in the art, or can be purchased from ABCR GmbH & Co. KG, Acros Organics, Aldrich Chemical Company, Accela ChemBio Inc., Darui Chemicals, and other companies.

Unless otherwise specified in the examples, the solution refers to an aqueous solution.

Unless otherwise specified in the examples, the reaction temperature is room temperature, e.g., 20° C. to 30° C.

Example 1

Preparation of Compound 1

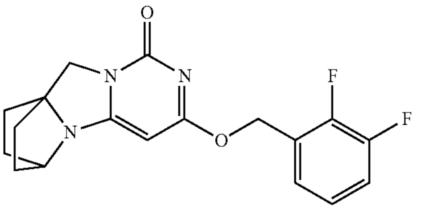

1

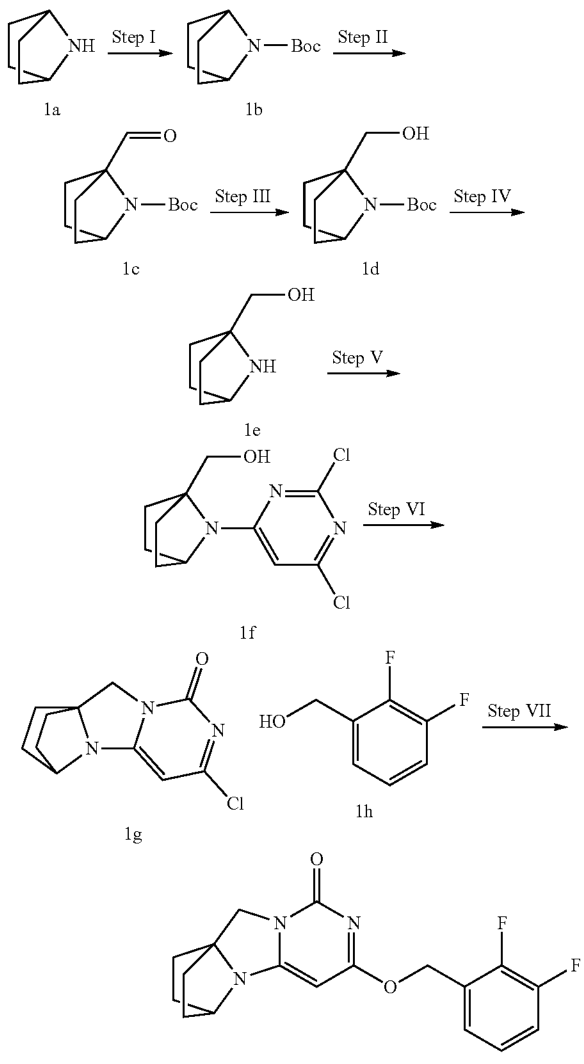

1a 1b 1c 1d 1e 1f 1g 1h

1

Step I: Preparation of Compound 1b

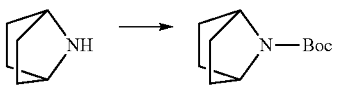

1a 1b

At room temperature, 7-azabicyclo[2.2.1]heptane 1a (4 g, 41.1 mmol) was dissolved in 300 mL of dichloromethane, followed by addition of triethylamine (6.3 g, 61.8 mmol) and di-tert-butyl dicarbonate (13.5 g, 61.8 mmol). The materials were stirred at room temperature and reacted for 4 h, and the reactant was extracted with dichloromethane (100 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=20:1) by the silica gel column chromatography to give a colorless, oily product 1b (10 g, yield: 100%). $^1H$ NMR (400 MHz, $CDCl_3$) δ 4.16 (s, 2H), 1.74-1.72 (m, 4H), 1.42 (s, 9H), 1.37-1.35 (m, 4H).

Step II: Preparation of Compound 1c

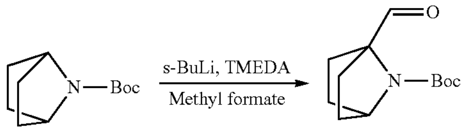

1b 1c

At room temperature, tert-butyl 7-azabicyclo[2.2.1]heptane-7-carboxylate 1b (10 g, 50.8 mmol) and TMEDA (7.1 g, 60.9 mmol) were dissolved in 200 mL of dry ether, followed by adding dropwise a solution of s-BuLi (1.3 M, 60.9 mmol) in hexane at −65° C. under nitrogen protection. After the materials were stirred and reacted for 30 min, a solution of methyl formate (3.65 g, 60.9 mmol) in ether was added dropwise. This mixture was stirred and reacted at −65° C. for 30 min, heated to 0° C., and reacted for 2 h. To the reaction mixture, 100 mL of saturated aqueous ammonium chloride solution was added, and extracted with ether (50 mL×3). The organic phases were combined, dried over anhydrous sodium sulfate, and filtered to remove the drying agent. The filtrate was concentrated under reduced pressure, and purified with an eluent system (petroleum ether/ethyl acetate=40:1) by the silica gel column chromatography to give a colorless, oily product 1c (8.14 g, yield: 71%). $^1H$ NMR (400 MHz, $CDCl_3$) δ 9.93 (s, 1H), 4.29 (s, 1H), 2.03-1.88 (m, 4H), 1.65-1.46 (m, 4H), 1.42 (s, 9H).

Step III: Preparation of Compound 1d

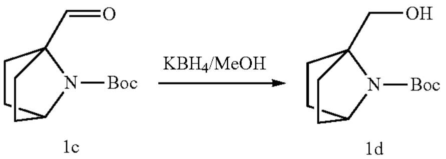 [SMILES: CC(C)(C)OC(=O)N1C2CCC1(C=O)CC2 ; CC(C)(C)OC(=O)N1C2CCC1(CO)CC2]

1c 1d

Tert-butyl 1-formyl-7-azabicyclo[2.2.1]heptane-7-carboxylate 1c (8.14 g, 36.1 mmol) was dissolved in 300 mL of methanol, to which $KBH_4$ (3.03 g, 54.2 mmol) was added in batch at 0° C. After the materials were stirred and reacted at room temperature for 1 h, the reactant was concentrated under reduced pressure, and extracted with dichloromethane (60 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=20/1) by the silica gel column chromatography to give a colorless, oily product 1d (6.53 g, yield: 79.5%). $^1H$ NMR (400 MHz, $CDCl_3$) δ4.96 (s, 1H), 4.24 (m, 1H), 3.90 (m, 2H), 1.89-1.77 (m, 4H), 1.48-1.35 (m, 13H).

Step IV: Preparation of Compound 1e

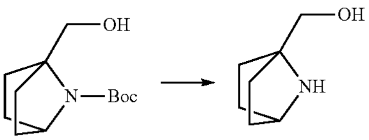

1d 1e

Tert-butyl 1-(hydroxymethyl)-7-azabicyclo[2.2.1]heptane-7-carboxylate 1d (6.53 g, 28.7 mmol) was dissolved in 100 mL of hydrochloric acid/ethanol (2M). After the materials were stirred and reacted at room temperature for 4 h, the reactant was concentrated under reduced pressure to give a yellow solid product 1e (4.72 g, yield: 100%).

$^1H$ NMR (400 MHz, DMSO) δ 9.04 (s, 2H), 3.98 (m, 1H), 3.73 (s, 2H), 1.98-1.82 (m, 4H), 1.69-1.53 (m, 4H).

Step V: Preparation of Compound 1f

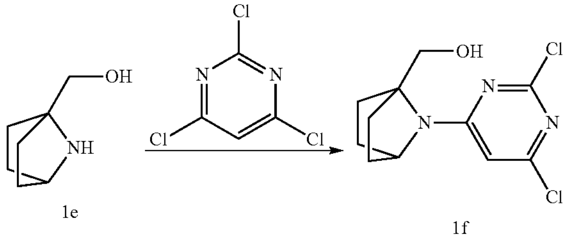

1e 1f

At room temperature, (7-azabicyclo[2.2.1]heptane-1-yl) methanol 1e (4.5 g, 35.5 mmol), 2,4,6-trichloropyrimidine (7.79 g, 42.6 mmol), and diisopropylethylamine (13.7 g, 106.5 mmol) were dissolved in 200 mL of acetonitrile, stirred overnight, concentrated under reduced pressure, and purified with an eluent system (petroleum ether/ethyl acetate=5:1) by the silica gel column chromatography to give a colorless solid product 1f (5.2 g, yield: 53%).

$^1H$ NMR (400 MHz, $CDCl_3$) δ 6.37 (s, 1H), 4.91 (m, 1H), 4.26 (m, 1H), 4.01 (m, 2H), 2.01-1.82 (m, 4H), 1.68-1.52 (m, 4H).

Step VI: Preparation of Compound 1g

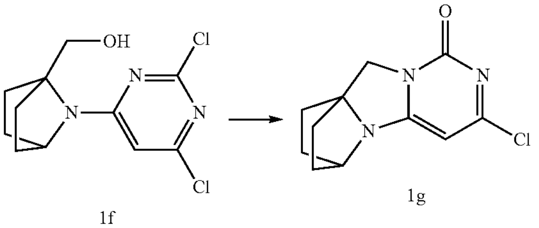 [SMILES: OCC12CCC(CC1)N2c1cc(Cl)nc(Cl)n1 ; O=c1nc(Cl)cc2n1CC13CCC(CC1)N23]

1f 1g

At room temperature, (7-(2,6-dichloropyrimidin-4-yl)-7-azabicyclo[2.2.1]heptan-1-yl) methanol 1f (5.46 g, 19.9 mmol) and triethylamine (6.0 g, 59.7 mmol) were dissolved in 100 mL of dry dichloromethane, to which MsCl (2.5 g, 21.9 mmol) was added dropwise at 0° C. After the materials were stirred and reacted at 0° C. for 1 h, the reactant was concentrated under reduced pressure, and dissolved in 100 mL of a mixed solvent of dioxane/water (1:1), to which potassium carbonate (8.2 g, 59.7 mmol) was added, and stirred at 90° C. overnight. Then the reactant was concentrated under reduced pressure, and purified with an eluent system (dichloromethane/methanol=20:1) by the silica gel column chromatography to give a colorless solid product 1g (2.2 g, yield: 46%).

$^1H$ NMR (400 MHz, DMSO) δ 6.10 (s, 1H), 4.42 (m, 1H), 3.95 (s, 2H), 1.94-1.89 (m, 2H), 1.78-1.69 (m, 6H).

Step VII: Preparation of Compound 1

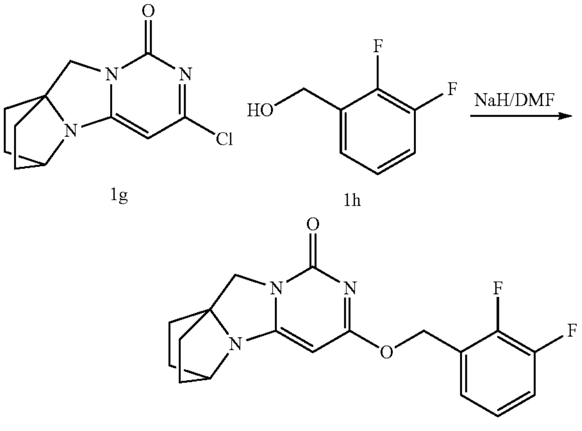

1g 1h

1

(2,3-Difluorophenyl) methanol 1h (46 mg, 0.32 mmol) was dissolved in 2 mL of dry N,N-dimethylformamide for 1 h, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 1 (31 mg, yield: 43%).

$^1H$ NMR (400 MHz, $CDCl_3$) δ 7.24-7.03 (m, 3H), 5.45 (s, 2H), 5.15 (s, 1H), 4.09 (m, 1H), 3.99 (s, 2H), 2.14-1.99 (m, 2H), 1.78-1.66 (m, 6H). MS (ESI): m/z 346.0 $[M+H]^+$.

Example 2 Preparation of Compound 2

2

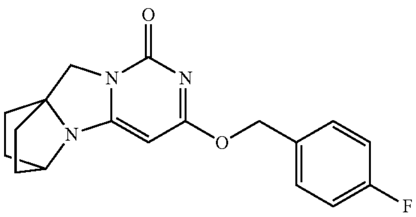

(4-Fluorophenyl) methanol (40 mg, 0.32 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 2 (40 mg, yield: 58%).

$^1$H NMR (400 MHz, $CDCl_3$) δ 7.43-7.40 (m, 2H), 7.08-7.04 (m, 2H), 5.37 (s, 2H), 5.17 (s, 1H), 4.11 (m, 1H), 4.01 (s, 2H), 2.10-2.06 (m, 2H), 1.82-1.67 (m, 6H). MS (ESI): m/z 328.0 $[M+H]^+$.

Example 3 Preparation of Compound 3

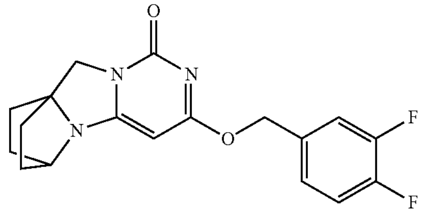

3

(3,4-Dichlorophenyl) methanol (46 mg, 0.32 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 3 (17 mg, yield: 23%).

$^1$H NMR (400 MHz, $CDCl_3$) δ 7.28-7.22 (m, 1H), 7.18-7.11 (m, 2H), 5.35 (s, 2H), 5.17 (s, 1H), 4.12 (m, 1H), 4.01 (s, 2H), 2.12-2.07 (m, 2H), 1.83-1.74 (m, 6H). MS (ESI): m/z 346.0 $[M+H]^+$.

Example 4 Preparation of Compound 4

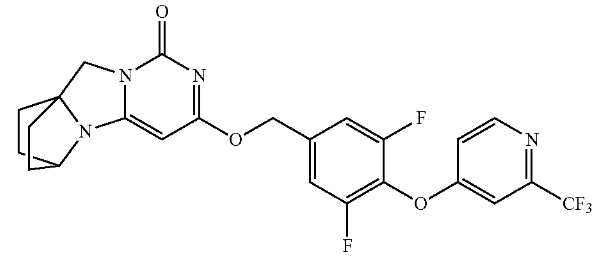

4

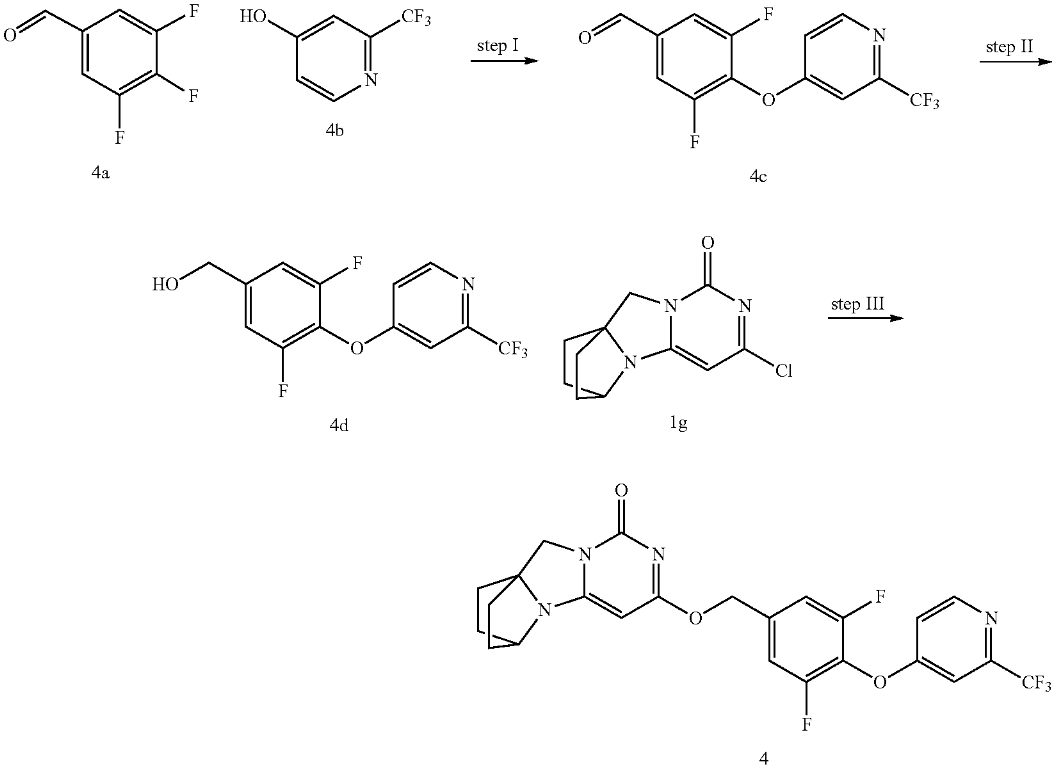

4a 4b 4c 4d 1g

4

Step I: Preparation of Compound 4c

At room temperature, 2-(trifluoromethyl)pyridin-4-ol 4b (0.85 g, 5.2 mmol), 3,4,5-trifluorobenzaldehyde (1 g, 6.2 mmol) and potassium carbonate (0.93 g, 6.76 mmol) were dissolved in 30 mL of N,N-dimethylformamide, and stirred and reacted at 90° C. for 1 h. The reactant was cooled to room temperature, then poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=5/1) by the silica gel column chromatography to give a yellow solid product 4c (1.47g, yield: 78.2%).

$^1$H NMR (400 MHz, $CDCl_3$) δ 9.97 (s, 1H), 8.65 (m, 1H), 7.63 (m, 2H), 7.27 (m, 1H), 7.01 (m, 1H).

Step II: Preparation of Compound 4d

At room temperature, 3,5-difluoro-4-((2-(trifluoromethyl) pyridin-4-yl)oxy)benzaldehyde 4c (1.47 g, 4.85 mmol) was dissolved in 50 mL of ethanol, to which $NaBH_4$ (184 mg, 4.85 mmol) was added at 0° C. The materials were stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=2:1) by the silica gel column chromatography to give a white solid product 4d (1.04 g, yield: 70.3%).

$^1$H NMR (400 MHz, $CDCl_3$) δ 8.59 (m, 1H), 7.24 (m, 1H), 7.11 (m, 2H), 6.99 (m, 1H), 4.75 (m, 2H), 2.19 (m, 1H).

Step III: Preparation of Compound 4 (3,5-Difluoro-4-((2-(trifluoromethyl)pyridin-4-yl)oxy)phenyl) methanol (77 mg, 0.25 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 5 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 4 (35 mg, yield: 33%).

$^1$H NMR (400 MHz, $CDCl_3$) δ 8.62 (m, 1H), 7.28 (s, 1H), 7.15 (m, 2H), 7.01 (m, 1H), 5.44 (s, 2H), 5.24 (s, 1H), 4.16 (m, 1H), 4.03 (s, 2H), 2.12-2.07 (m, 2H), 1.83-1.79 (m, 6H). MS (ESI): m/z 506.9 $[M+H]^+$.

Example 5 Preparation of Compound 5

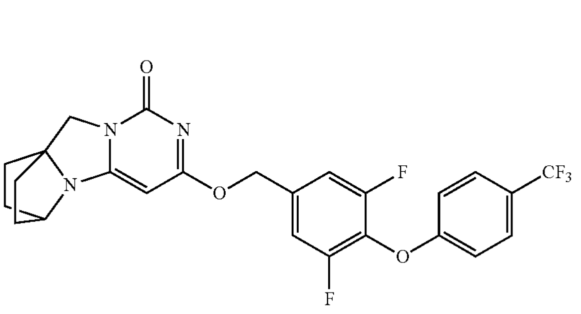

5

-continued

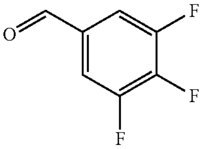

4a

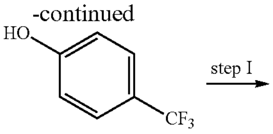

5a

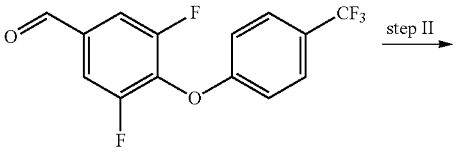

5b

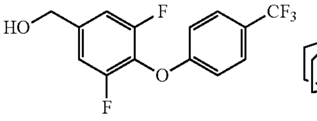

5c

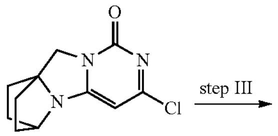

1g

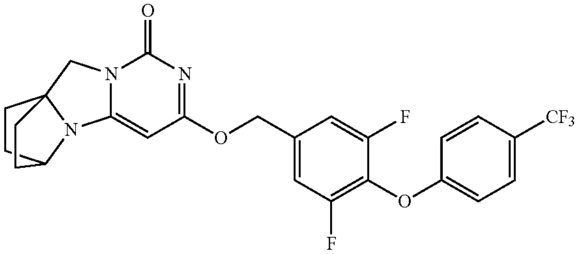

5

Step I: Preparation of Compound 5b

At room temperature, 4-(trifluoromethyl) phenol 5a (0.84 g, 5.2 mmol), 3,4,5-trifluorobenzaldehyde 4a (1 g, 6.2 mmol) and potassium carbonate (0.93 g, 6.76 mmol) were dissolved in 30 mL N,N-dimethylformamide, and stirred and reacted at 90° C. for 1 h. The reactant was cooled to room temperature, then poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=5/1) by the silica gel column chromatography to give a yellow solid product 5b (1.33 g, yield: 71.0%).

$^1$H NMR (400 MHz, $CDCl_3$) δ 9.94 (m, 1H), 7.59 (m, 4H), 7.04 (m, 2H).

Step II: Preparation of Compound 5c

At room temperature, 3,5-difluoro-4-(4-(trifluoromethyl) phenoxy)benzaldehyde 5b (1.33 g, 4.4 mmol) was dissolved in 50 mL of methylethanol, to which $NaBH_4$ (166 mg, 4.4 mmol) was added at 0° C. The materials were stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=2/1) by the silica gel column chromatography to give a colorless, oily product 5c (0.85g, yield: 63.6%).

$^1$H NMR (400 MHz, $CDCl_3$) δ 7.57 (m, 2H), 7.09-7.00 (m, 4H), 4.72 (m, 2H), 2.03 (m, 1H).

Step III: Preparation of Compound 5

3,5-Difluoro-4-(4-(trifluoromethyl) phenoxy)phenyl) methanol 5c (64 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 5 (17 mg, yield: 16%).

$^{1}$H NMR (400 MHz, $CDCl_3$) δ 7.59 (m, 2H), 7.12-7.02 (m, 4H), 5.42 (s, 2H), 5.23 (s, 1H), 4.15 (m, 1H), 4.03 (s, 2H), 2.12 (m, 2H), 1.87-1.74 (m, 6H). MS (ESI): m/z 506.0 $[M+H]^+$.

Example 6 Preparation of Compound 6

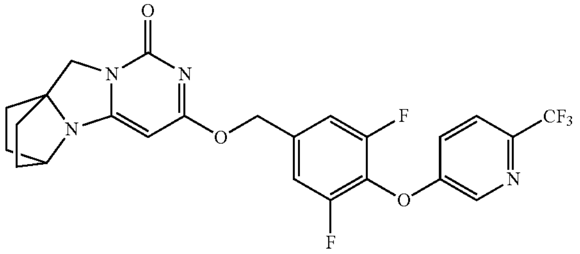

6

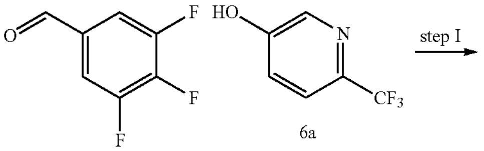

4a 6a

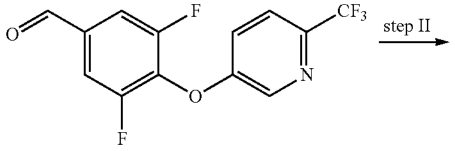

6b

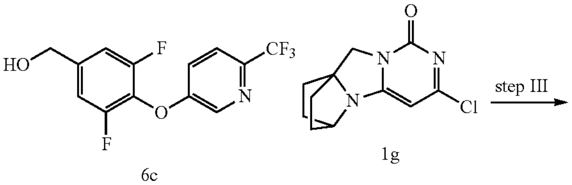

6c 1g

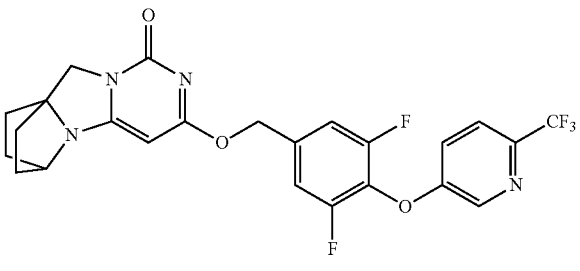

6

Step I: Preparation of Compound 6b

At room temperature, 6-(trifluoromethyl)pyridin-3-ol 6a (0.85 g, 5.2 mmol), 3,4,5-trifluorobenzaldehyde 4a (1 g, 6.2 mmol) and potassium carbonate (0.93 g, 6.76 mmol) were dissolved in 30 mL of N,N-dimethylformamide, and stirred and reacted at 90° C. for 1 h. The reactant was cooled to room temperature, then poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=5/1) by the silica gel column chromatography to give a yellow solid product 6b (1.34 g, yield: 84.6%).

Step II: Preparation of Compound 6c

At room temperature, 3,5-difluoro-4-((6-(trifluoromethyl) pyridin-3-yl)oxy)benzaldehyde 6b (1.34 g, 4.4 mmol) was dissolved in 50 mL of methanol, to which $NaBH_4$ (167 mg, 4.4 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=2:1) by the silica gel column chromatography to give a colorless, oily product 6c (0.77 g, yield: 57.4%).

$^{1}$H NMR (400 MHz, $CDCl_3$) δ 8.46 (s, 1H), 7.63 (m, 1H), 7.30 (m, 1H), 7.09 (m, 2H), 4.73 (m, 2H), 2.40 (m, 1H).

Step III: Preparation of Compound 6

(3,5-Difluoro-4-((6-(trifluoromethyl)pyridin-3-yl)oxy) phenyl) methanol 6c (50 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 6 (31 mg, yield: 29%).

$^{1}$H NMR (400 MHz, $CDCl_3$) δ 8.51 (m, 1H), 7.65 (m, 1H), 7.31 (m, 1H), 7.13 (m, 2H), 5.42 (s, 2H), 5.23 (s, 1H), 4.15 (m, 1H), 4.03 (s, 2H), 2.12-2.06 (m, 2H), 1.85-1.70 (m, 6H). MS (ESI): m/z 507.0 $[M+H]^+$.

Example 7 Preparation of Compound 7

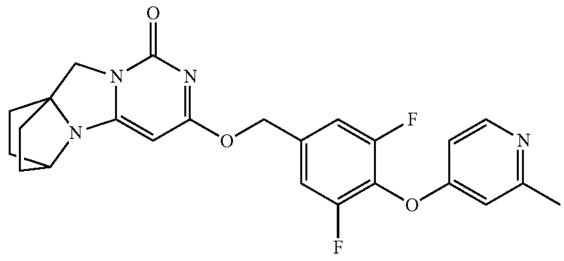

7

-continued

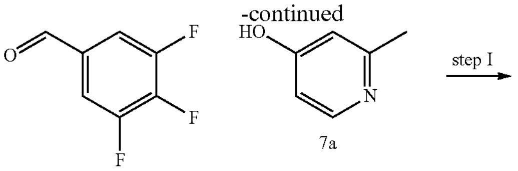

4a 7a

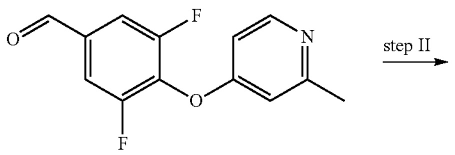

7b

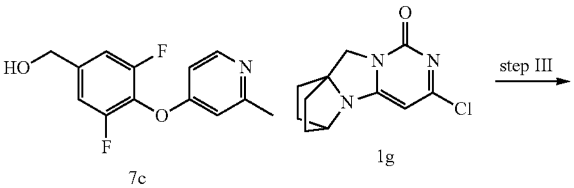

7c 1g

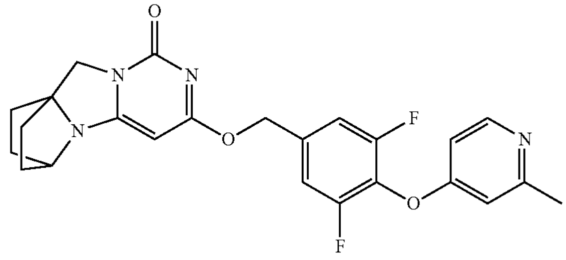

7

Step I: Preparation of Compound 7b

At room temperature, 6-methylpyridin-4-ol 7a (0.5 g, 4.6 mmol), 3,4,5-trifluorobenzaldehyde 4a (0.88 g, 5.5 mmol) and potassium carbonate (0.823 g, 5.95 mmol) were dissolved in 30 mL of N,N-dimethylformamide, and stirred and reacted at 90° C. for 2 h. The reactant was cooled to room temperature, then poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 7b (0.4 g, yield: 33.8%).

$^1$H NMR (400 MHz, $CDCl_3$) δ 9.94 (s, 1H), 8.39 (m, 1H), 7.62-7.56 (m, 2H), 6.70-6.66 (m, 2H), 2.52 (s, 3H).

Step II: Preparation of Compound 7c

At room temperature, 3,5-difluoro-4-((2-methylpyridin-4-yl)oxy)benzaldehyde 7b (0.4 g, 1.86 mmol) was dissolved in 50 mL of methanol, to which $NaBH_4$ (71 mg, 1.86 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 7c (0.40 g, yield: 85.7%).

$^1$H NMR (400 MHz, $CDCl_3$) δ 8.29 (m, 1H), 7.07 (m, 2H), 6.70-6.64 (m, 2H), 4.73 (s, 2H), 3.20 (m, 1H), 2.50 (s, 3H).

Step III: Preparation of Compound 7

(3,5-Difluoro-4-((2-methylpyridin-4-yl)oxy)phenyl) methanol 7c (53 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 7 (17 mg, yield: 18%).

$^1$H NMR (400 MHz, $CDCl_3$) δ 8.38 (m, 1H), 7.10 (m, 2H), 6.69 (m, 2H), 5.42 (s, 2H), 5.23 (s, 1H), 4.15 (m, 1H), 4.03 (s, 2H), 2.53 (s, 3H), 2.21-2.07 (m, 2H), 1.88-1.70 (m, 6H). MS (ESI): m/z 453.0 [M+H]$^+$.

Example 8 Preparation of Compound 8

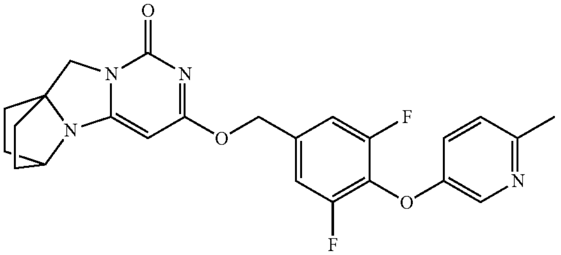

8

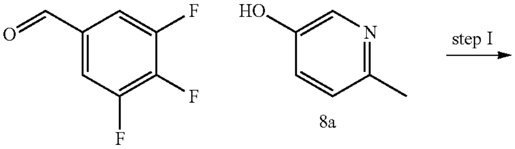

4a 8a

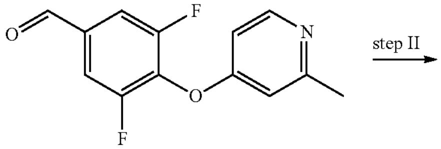

8b

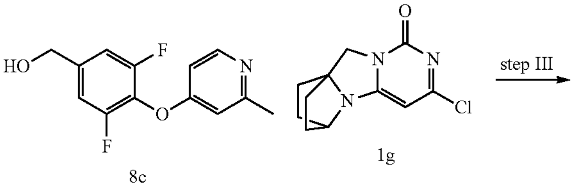

8c 1g

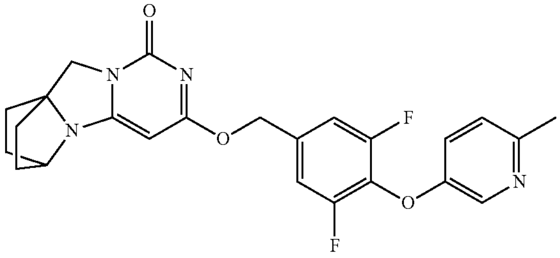

8

Step I: Preparation of Compound 8b

At room temperature, 6-methylpyridin-3-ol 8a (0.57 g, 5.2 mmol), 3,4,5-trifluorobenzaldehyde 4a (1 g, 6.2 mmol) and potassium carbonate (0.93 g, 6.76 mmol) were dissolved in 30 mL of N,N-dimethylformamide, and stirred and reacted at 90° C. for 1 h. The reactant was cooled to room temperature, then poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 8b (0.91g, yield: 69.4%).

$^1$H NMR (400 MHz, $CDCl_3$) δ 9.92 (s, 1H), 8.28 (s, 1H), 7.62-7.49 (m, 2H), 7.18-7.10 (m, 2H), 2.54 (s, 3H).

Step II: Preparation of Compound 8c

At room temperature, 3,5-difluoro-4-((2-methylpyridin-4-yl)oxy)benzaldehyde 8b (0.91 g, 4.3 mmol) was dissolved in 50 mL of methanol, to which $NaBH_4$ (161 mg, 4.3 mmol) was added at 0° C., stirred and reacted at room temperature for 0.5h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 8c (0.89 g, yield: 82.5%).

$^1$H NMR (400 MHz, $CDCl_3$) § 8.20 (m, 1H), 7.16-6.98 (m, 4H), 4.69 (m, 2H), 2.88 (m, 1H), 2.50 (s, 3H).

Step III: Preparation of Compound 8

(3,5-Difluoro-4-((2-methylpyridin-4-yl)oxy)phenyl) methanol 8c (53 mg, 0.21 mmol) was dissolved in 2 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 8 (20 mg, yield: 21%).

$^1$H NMR (400 MHz, $CDCl_3$) § 8.30 (m, 1H), 7.18-7.04 (m, 4H), 5.40 (s, 2H), 5.22 (s, 1H), 4.15 (m, 1H), 4.03 (s, 2H), 2.54 (s, 3H), 2.11 (m, 2H), 1.86-1.74 (m, 6H). MS (ESI): m/z 453.0 [M+H]$^+$.

Example 9 Preparation of Compound 9

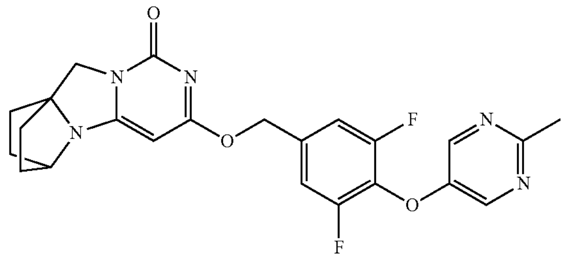

9

-continued

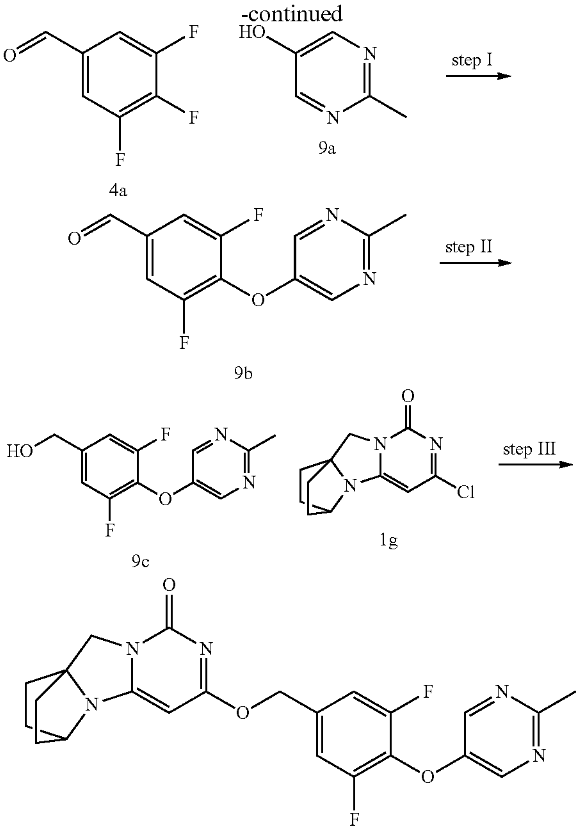

4a
9a
9b
9c
1g
9

Step I: Preparation of Compound 9b

At room temperature, 2-methylpyrimidin-5-ol 9a (0.25 g, 2.27 mmol), 3,4,5-trifluorobenzaldehyde 4a (0.44 g, 2.72 mmol) and potassium carbonate (0.41 g, 2.95 mmol) were dissolved in 30 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10:1) by the silica gel column chromatography to give a yellow solid product 9b (0.24 g, yield: 34.8%).

$^1$H NMR (400 MHz, $CDCl_3$) δ 9.93 (s, 1H), 8.39 (s, 2H), 7.64-7.54 (m, 2H), 2.72 (s, 3H).

Step II: Preparation of Compound 9c

At room temperature, 3,5-difluoro-4-((2-methylpyrimidin-5-yl)oxy)benzaldehyde 9b (0.24 g, 0.79 mmol) was dissolved in 50 mL of methanol, to which $NaBH_4$ (30 mg, 0.79 mmol) was added at 0° C., stirred and reacted at room temperature for 0.5 h, concentrated under reduced pressure, added with water, and extracted with ethyl acetate (100 mL×2). The organic phases were combined, washed with sodium chloride solution, dried over anhydrous sodium sulfate, and filtered to remove the drying agent. The filtrate was concentrated under reduced pressure, and purified with an eluent system (petroleum ether/ethyl acetate=4:1) by the silica gel column chromatography to give a colorless, oily product 9c (0.17 g, yield: 85.4%).

$^1$H NMR (400 MHz, $CDCl_3$) δ 8.33 (s, 2H), 7.04 (m, 2H), 4.71 (m, 2H), 2.70 (s, 3H).

Step III: Preparation of Compound 9

(3,5-Difluoro-4-((2-methylpyrimidin-5-yl)oxy)phenyl) methanol 9c (53 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 9 (18 mg, yield: 19%).

$^1$H NMR (400 MHz, $CDCl_3$) δ 8.34 (s, 2H), 7.09 (m, 2H), 5.37 (s, 2H), 5.20 (s, 1H), 4.12 (m, 1H), 3.99 (s, 2H), 2.69 (s, 3H), 2.13-2.03 (m, 2H), 1.81-1.71 (m, 6H). MS (ESI): m/z 454.0 [M+H]$^+$.

Example 10 Preparation of Compound 10

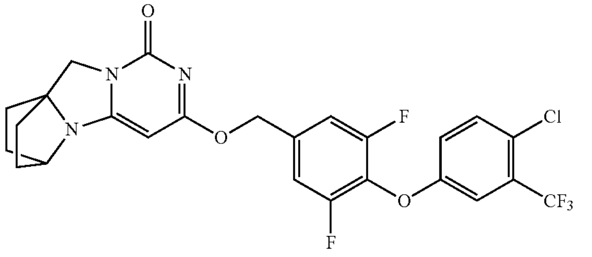

10

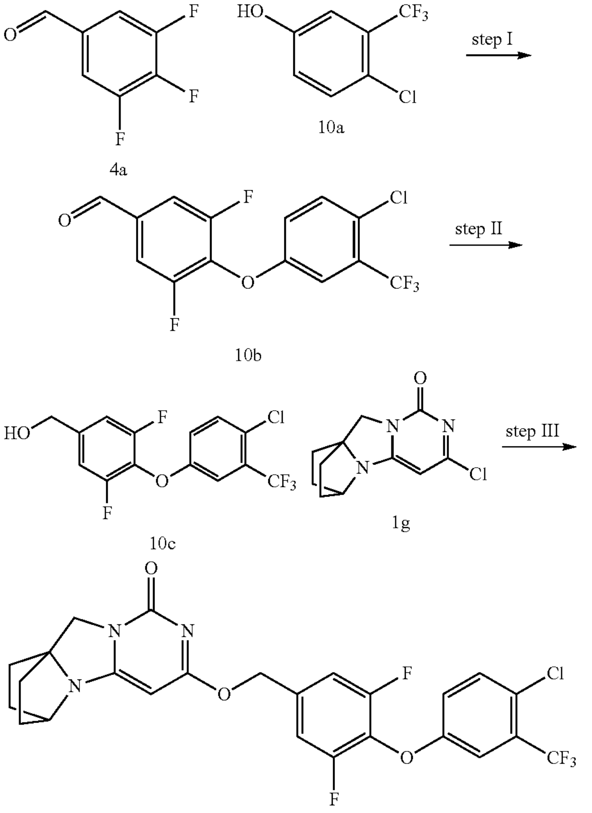

4a 10a 10b 10c 1g 10

Step I: Preparation of Compound 10b

At room temperature, 4-chloro-3-(trifluoromethyl) phenol 10a (0.5 g, 2.54 mmol), 3,4,5-trifluorobenzaldehyde 4a (0.45 g, 2.8 mmol) and potassium carbonate (0.46 g, 3.3 mmol) were dissolved in 30 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 10b (0.6 g, yield: 70.1%).

$^1$H NMR (400 MHz, $CDCl_3$) δ 9.94 (s, 1H), 7.64-7.55 (m, 2H), 7.45 (m, 1H), 7.31 (m, 1H), 7.05 (m, 1H).

Step II: Preparation of Compound 10c

At room temperature, 4-(4-chloro-3-(trifluoromethyl) phenoxy)-3,5-difluorobenzaldehyde 10b (0.6 g, 1.78 mmol) was dissolved in 50 mL of methanol, to which $NaBH_4$ (67 mg, 1.78 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a white solid product 10c (0.28 g, yield: 46.4%).

$^1$H NMR (400 MHz, $CDCl_3$) δ 7.41 (m, 1H), 7.28 (m, 1H), 7.08-7.00 (m, 3H), 4.73 (m, 2H), 1.94 (m, 1H).

Step III: Preparation of Compound 10

(4-(4-Chloro-3-(trifluoromethyl) phenoxy)-3,5-difluorophenyl) methanol 10c (71 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 10 (28 mg, yield: 25%).

$^1$H NMR (400 MHz, $CDCl_3$) δ 7.41 (m, 1H), 7.29 (m, 1H), 7.08 (m, 2H), 7.01 (m, 1H), 5.38 (s, 2H), 5.20 (s, 1H), 4.13 (m, 1H), 4.00 (s, 2H), 2.19-2.08 (m, 2H), 1.84-1.74 (m, 6H). MS (ESI): m/z 539.9 [M+H]$^+$.

Example 11 Preparation of Compound 11

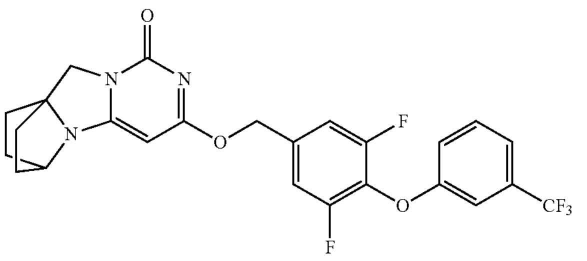

11

-continued

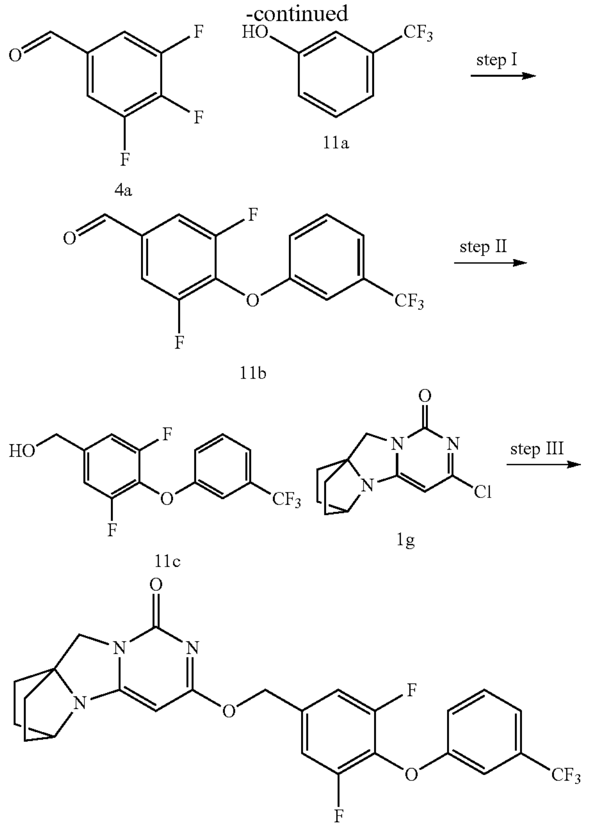

4a 11a 11b 11c 1g 11

Step I: Preparation of Compound 11b

At room temperature, 3-(trifluoromethyl) phenol 11a (1 g, 6.17 mmol), 3,4,5-trifluorobenzaldehyde 4a (1.09 g, 6.79 mmol) and potassium carbonate (1.1 g, 8.02 mmol) were dissolved in 30 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 11b (1.7 g, yield: 82.5%).

$^1$H NMR (400 MHz, $CDCl_3$) δ 9.94 (s, 1H), 7.63-7.55 (m, 2H), 7.46 (m, 1H), 7.39 (m, 1H), 7.21 (s, 1H), 7.13 (m, 1H).

Step II: Preparation of Compound 11c

At room temperature, 3,5-difluoro-4-(3-(trifluoromethyl) phenoxy)benzaldehyde 11b (1.7 g, 5.6 mmol) was dissolved in 50 mL of methanol, to which $NaBH_4$ (213 mg, 5.6 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 11c (1.27 g, yield: 74.5%).

Step III: Preparation of Compound 11

(3,5-Difluoro-4-(3-(trifluoromethyl) phenoxy)phenyl) methanol 11c (71 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 11 (33 mg, yield: 31%).

$^1$H NMR (400 MHz, $CDCl_3$) δ 7.44 (m, 1H), 7.36 (m, 1H), 7.22 (s, 1H), 7.11 (m, 3H), 5.42 (s, 2H), 5.23 (s, 1H), 4.15 (m, 1H), 4.03 (s, 2H), 2.12 (m, 2H), 1.83-1.77 (m, 6H). MS (ESI): m/z 505.9 $[M+H]^+$.

Example 12 Preparation of Compound 12

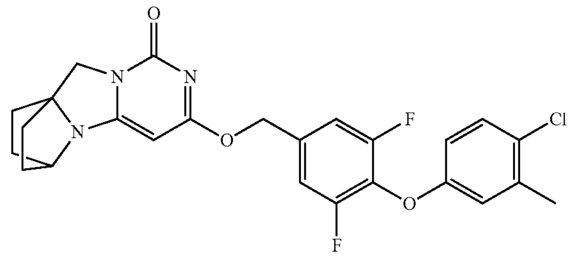

12

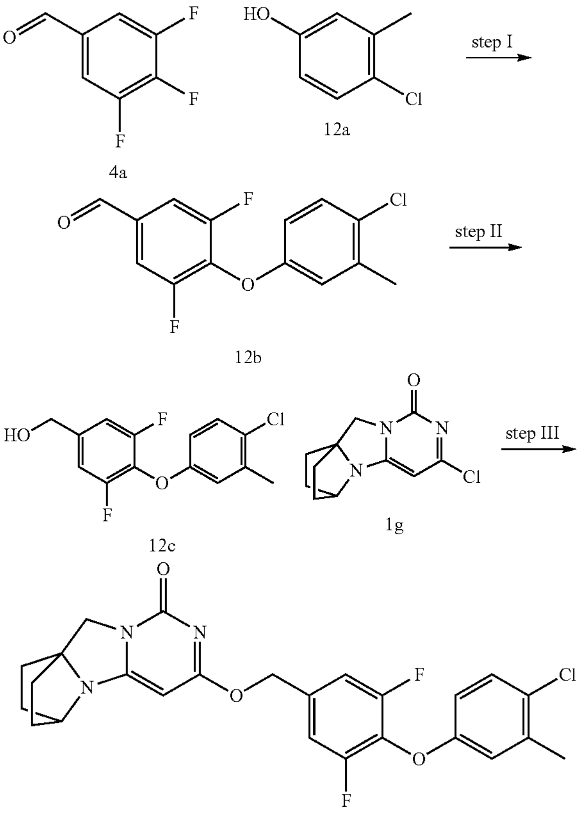

12a 4a 12b 12c 1g 12

Step I: Preparation of Compound 12b

At room temperature, 4-chloro-3-methylphenol 12a (1 g, 7.0 mmol), 3,4,5-trifluorobenzaldehyde 4a (1.2 g, 7.7 mmol)

and potassium carbonate (1.3 g, 9.1 mmol) were dissolved in 30 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 12b (1.2 g, yield: 54.5%).

$^1$H NMR (400 MHz, $CDCl_3$) δ 9.92 (s, 1H), 7.61-7.51 (m, 2H), 7.30-7.23 (m, 1H), 6.85 (m, 1H), 6.73 (m, 1H), 2.34 (s, 3H).

Step II: Preparation of Compound 12c

At room temperature, 4-(4-chloro-3-methylphenoxy)-3,5-difluorobenzaldehyde 12b (1.2 g, 4.2 mmol) was dissolved in 50 mL of methanol, to which $NaBH_4$ (161 mg, 4.2 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 12c (0.89 g, yield: 74.4%).

Step III: Preparation of Compound 12

4-(4-Chloro-3-methylphenoxy)-3,5-difluorophenyl) methanol 12c (59 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 12 (29 mg, yield: 31%).

$^1$H NMR (400 MHz, $CDCl_3$) δ 7.25 (m, 1H), 7.08 (m, 2H), 6.84 (m, 1H), 6.73 (m, 1H), 5.40 (s, 2H), 5.22 (s, 1H), 4.15 (m, 1H), 4.03 (s, 2H), 2.35 (s, 3H), 2.12 (m, 2H), 1.87-1.74 (m, 6H). MS (ESI): m/z 486.0 $[M+H]^+$.

Example 13: Preparation of Compound 13

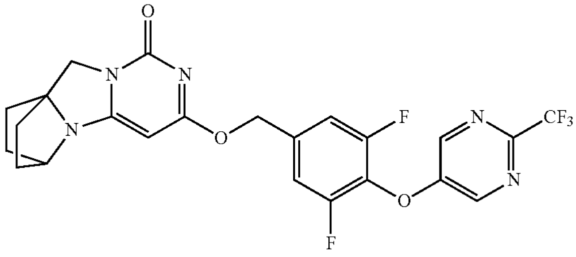

13

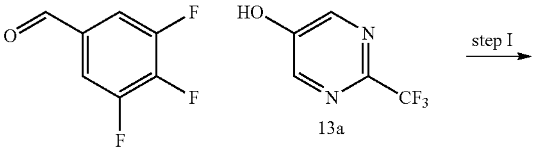

4a 13a

-continued

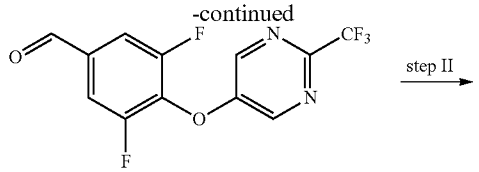

13b

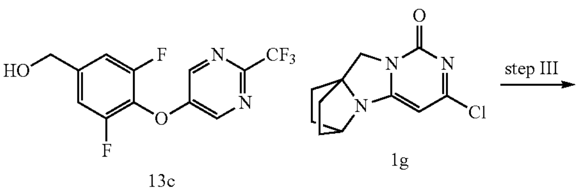

13c 1g

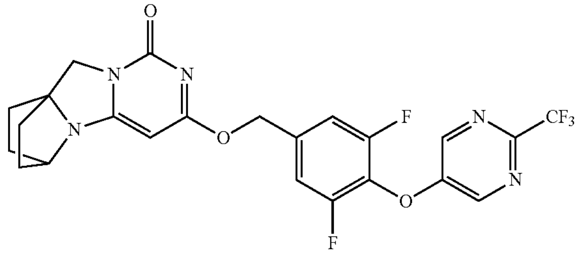

13

Step I: Preparation of Compound 13b

At room temperature, 2-(trifluoromethyl)pyrimidin-5-ol 13a (0.25 g, 1.52 mmol), 3,4,5-trifluorobenzaldehyde 4a (0.29 g, 1.83 mmol) and potassium carbonate (0.27 g, 1.98 mmol) were dissolved in 20 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 13b (0.24 g, yield: 52.0%).

$^1$H NMR (400 MHz, $CDCl_3$) δ 9.97 (s, 1H), 8.59 (s, 2H), 7.69-7.54 (m, 2H).

Step II: Preparation of Compound 13c

At room temperature, 3,5-difluoro-4-((2-(trifluoromethyl) pyrimidin-5-yl)oxy)benzaldehyde 13b (0.24 g, 0.79 mmol) was dissolved in 50 mL of methanol, to which $NaBH_4$ (30 mg, 0.79 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 13c (0.12 g, yield: 49.6%).

$^1$H NMR (400 MHz, $CDCl_3$) δ 8.54 (s, 2H), 7.12 (m, 2H), 4.74 (m, 2H), 2.23 (m, 1H).

Step III: Preparation of Compound 13

(3,5-Difluoro-4-((2-(trifluoromethyl)pyrimidin-5-yl)oxy) phenyl) methanol 13c (64 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 13 (18 mg, yield: 17%).

$^1$H NMR (400 MHz, $CDCl_3$) δ 8.58 (s, 2H), 7.17 (m, 2H), 5.43 (s, 2H), 5.24 (s, 1H), 4.16 (m, 1H), 4.03 (s, 2H), 2.13 (m, 2H), 1.88-1.76 (m, 6H).

MS (ESI): m/z 508.1 [M+H]$^+$.

Example 14: Preparation of Compound 14

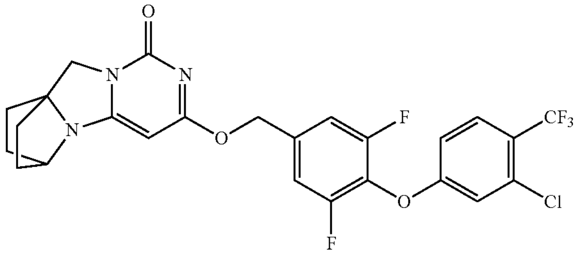

14

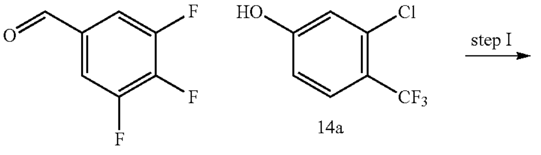

4a

14a

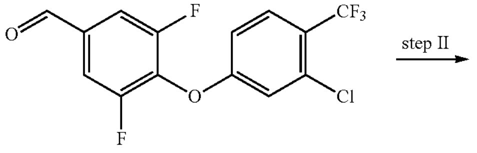

14b

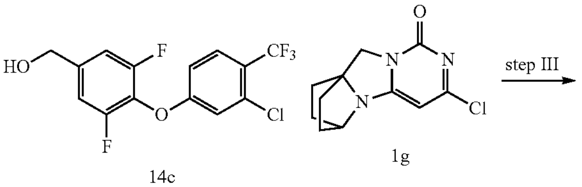

14c

1g

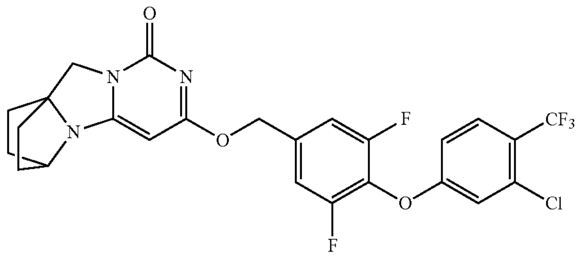

14

Step I: Preparation of Compound 14b

At room temperature, 3-chloro-4-(trifluoromethyl) phenol 14a (0.25 g, 1.27 mmol), 3,4,5-trifluorobenzaldehyde 4a (0.22 g, 1.4 mmol) and potassium carbonate (0.23 g, 1.65 mmol) were dissolved in 20 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 14b (0.32 g, yield: 74.0%).

$^1$H NMR (400 MHz, $CDCl_3$) δ 9.95 (s, 1H), 7.69-7.56 (m, 3H), 7.10 (m, 1H), 6.92 (m, 1H).

Step II: Preparation of Compound 14c

At room temperature, 4-(3-chloro-4-(trifluoromethyl) phenoxy)-3,5-difluorobenzaldehyde 14b (0.32 g, 0.94 mmol) was dissolved in 50 mL of methanol, to which $NaBH_4$ (36 mg, 0.94 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a white solid product 14c (0.15 g, yield: 47.1%).

$^1$H NMR (400 MHz, $CDCl_3$) δ 7.62 (m, 1H), 7.13-7.00 (m, 3H), 6.90 (m, 1H), 4.74 (m, 2H), 1.88 (m, 1H).

Step III: Preparation of Compound 14

(4-(3-Chloro-4-(trifluoromethyl) phenoxy)-3,5-difluorophenyl) methanol 14c (71 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 14 (12 mg, yield: 10%).

$^1$H NMR (400 MHz, $CDCl_3$) δ 7.64 (m, 1H), 7.10 (m, 3H), 6.91 (m, 1H), 5.41 (s, 2H), 5.23 (s, 1H), 4.15 (m, 1H), 4.03 (s, 2H), 2.19-2.04 (m, 2H), 1.83-1.75 (m, 6H). MS (ESI): m/z 539.9 [M+H]$^+$.

Example 15 Preparation of Compound 15

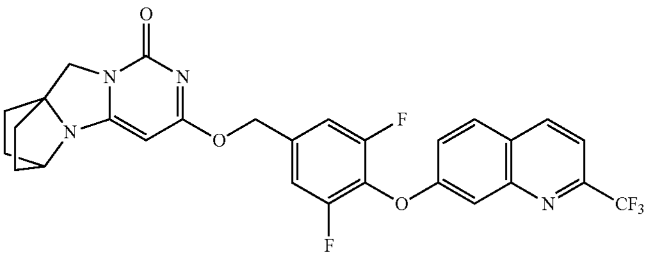

15

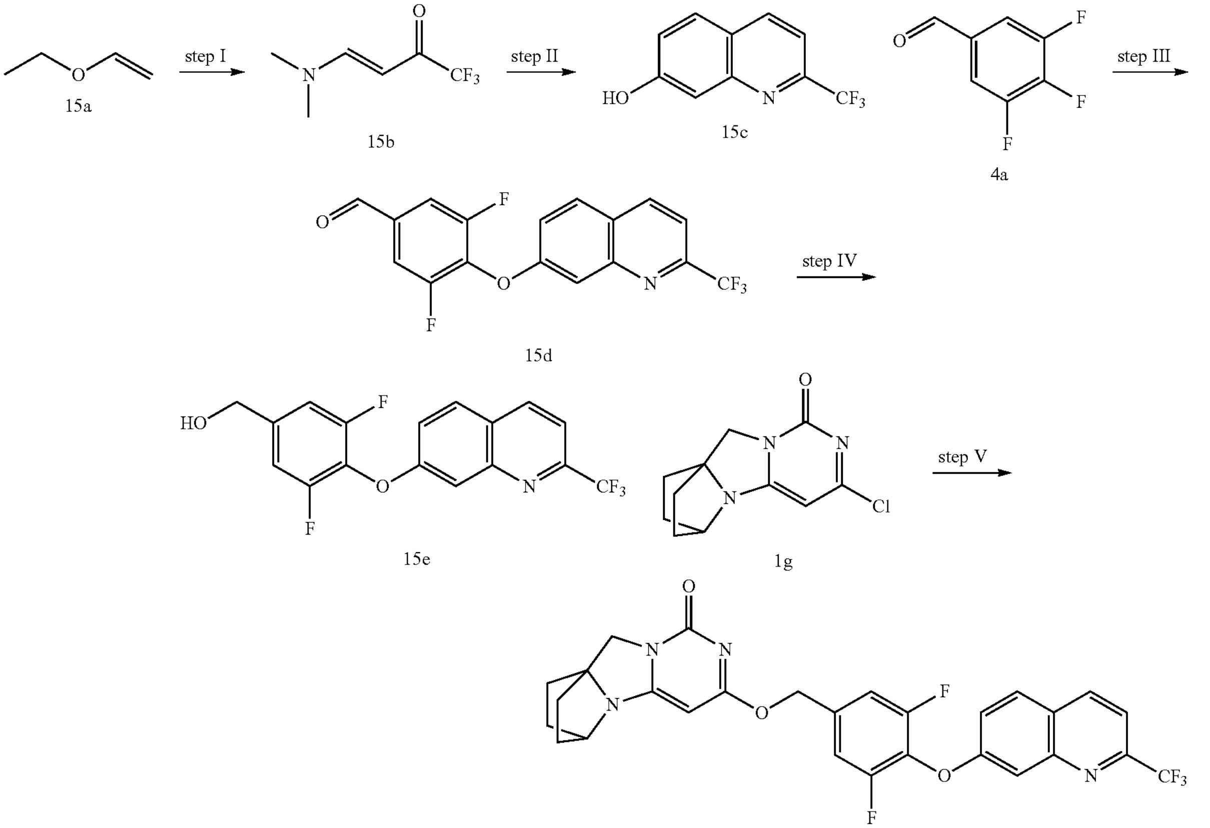

15a 15b 15c 4a 15d 15e 1g 15

Step I: Preparation of Compound 15b

Ethoxyethylene 15a (1 g, 13.9 mmol) and pyridine (1.65 g, 20.9 mmol) were dissolved in mL of dichloromethane, and trifluoroacetic anhydride was added at 0° C. under nitrogen protection. The materials were stirred and reacted for 20 min, heated to room temperature, and reacted for 2 h. The reaction mixture was cooled to −20° C., to which dimethylamine was added dropwise within 10 min, heated again to room temperature, and reacted for 2 h. The reaction was quenched with water. The reactant was extracted with dichloromethane (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a white solid product 15b (540 mg, yield: 23.1%).

$^1$H NMR (400 MHz, $CDCl_3$) δ 7.85 (m, 1H), 5.26 (m, 1H), 3.21 (s, 3H), 2.95 (s, 3H).

Step II: Preparation of Compound 15c

At room temperature, (E)-4-(dimethylamino)-1,1,1-trifluorobut-3-en-2-one 15b (0.54 g, 2.98 mmol) was dissolved in 20 mL of dichloroethane, and a solution of $Tf_2O$ in dichloroethane (5 mL) was added dropwise at 0° C., followed by adding a solution of 3-aminophenol in dichloroethane (10 mL). The materials were stirred and reacted at 40° C. for 2 h, and filtered to give a white solid product 15c (275 mg, 57.4%).

$^1$H NMR (400 MHz, MeOD) δ 8.43 (m, 1H), 7.90 (m, 1H), 7.62 (m, 1H), 7.40 (m, 1H), 7.32 (m, 1H).

Step III: Preparation of Compound 15d

At room temperature, 2-(trifluoromethyl) quinolin-7-ol 15c (0.37 g, 1.71 mmol), 3,4,5-trifluorobenzaldehyde 4a (0.28 g, 1.71 mmol) and potassium carbonate (0.71 g, 5.13 mmol) were dissolved in 20 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=5/1) by the silica gel column chromatography to give a white solid product 15d (310 mg, 51.5%).

$^1$H NMR (400 MHz, $CDCl_3$) δ 9.97 (s, 1H), 8.36 (m, 1H), 7.96 (m, 1H), 7.69 (m, 1H), 7.62 (m, 3H), 7.40 (s, 1H).

Step IV: Preparation of Compound 15e

At room temperature, 3,5-difluoro-4-((2-(trifluoromethyl) quinolin-7-yl)oxy)benzaldehyde 15d (0.31 g, 0.88 mmol) was dissolved in 20 mL of methanol, to which $NaBH_4$ (33 mg, 0.88 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 15e (230 mg, 74.6%).

Step V: Preparation of Compound 15

(3,5-Difluoro-4-((2-(trifluoromethyl) quinolin-7-yl)oxy) phenyl) methanol 15e (75 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction.and purified with an eluent system (dichloromethane/methanol=20:1) by the silica gel' column chromatography to give a white solid product 15 (18 mg, yield: 17%).

$^1$H NMR (400 MHz, $CDCl_3$) δ 8.33 (m, 1H), 7.92 (m, 1H), 7.65 (m, 1H), 7.60 (m, 1H), 7.36 (s, 1H), 7.13 (m, 2H), 5.40 (s, 2H), 5.23 (s, 1H), 4.14 (m, 1H), 4.02 (s, 2H), 2.11 (m, 2H), 1.79 (m, 6H). MS (ESI): m/z 557.0 $[M+H]^+$.

Example 16 Preparation of Compound 16

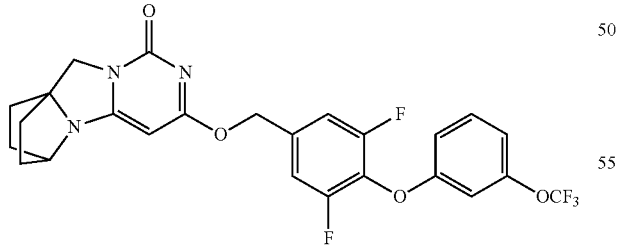

16

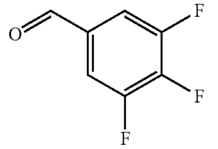

4a

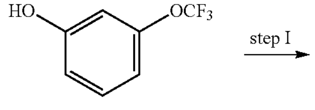

16a

-continued

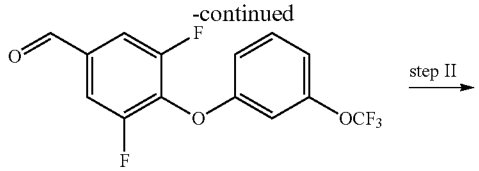

16b

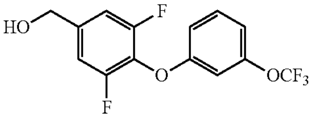

16c

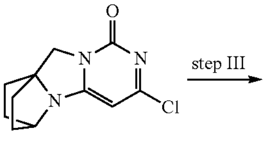

1g

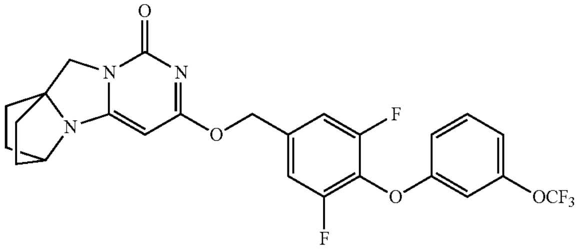

16

Step I: Preparation of Compound 16b

At room temperature, 3-(trifluoromethoxy) phenol 16a (0.50 g, 2.8 mmol), 3,4,5-trifluorobenzaldehyde 4a (0.5 g, 2.8 mmol) and potassium carbonate (0.5 g, 3.64 mmol) were dissolved in 30 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a white solid product 16b (0.73 g, yield: 81.4%).

$^1$H NMR (400 MHz, $CDCl_3$) δ 9.94 (s, 1H), 7.64-7.54 (m, 2H), 7.34 (m, 1H), 7.00 (m, 1H), 6.87 (m, 2H).

Step II: Preparation of Compound 16c

At room temperature, 4-(3-(trifluoromethoxy) phenoxy)-3,5-difluorobenzaldehyde 16b (0.73 g, 2.28 mmol) was dissolved in 50 mL of methanol, to which $NaBH_4$ (86 mg, 2.28 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 16c (0.57g, yield: 71.2%).

$^1$H NMR (400 MHz, $CDCl_3$) δ 7.30 (m, 1H), 7.06 (m, 2H), 6.94 (m, 1H), 6.85 (m, 1H), 6.81 (s, 1H), 4.72 (m, 2H), 1.94 (m, 1H).

Step III: Preparation of Compound 16

4-(3-(Trifluoromethoxy) phenoxy)-3,5-difluorophenyl) methanol 16c (67 mg, 0.21 mmol) was dissolved in 5 mL of dry N,N-dimethylformamide, to which sodium hydride (60% in mineral oil, 17 mg, 0.42 mmol) was added at 0° C.

After the materials were stirred and reacted at room temperature for 20 min, Compound 1g (50 mg, 0.21 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 16 (25 mg, yield: 23%).

$^1$H NMR (400 MHz, $CDCl_3$) δ 7.29 (m, 1H), 7.07 (m, 2H), 6.93 (m, 1H), 6.83 (m, 2H), 5.38 (s, 2H), 5.20 (s, 1H), 4.12 (m, 1H), 4.00 (s, 2H), 2.08 (m, 2H), 1.83-1.73 (m, 6H). MS (ESI): m/z 522.0 $[M+H]^+$.

Example 17 Preparation of Compound 17

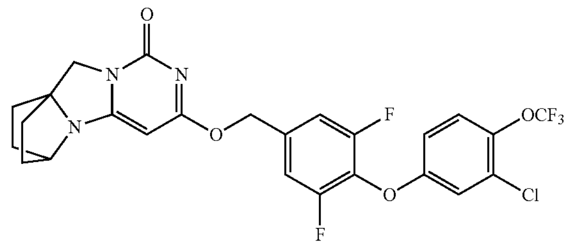

17

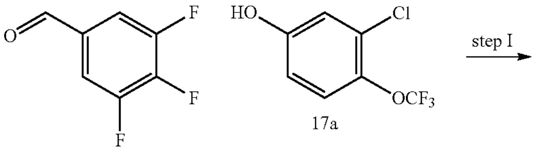

4a

17a

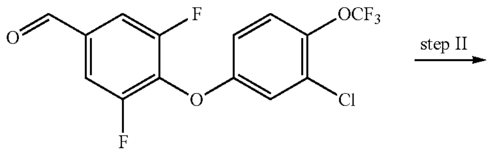

17b

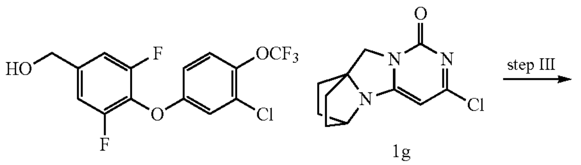

17c

1g

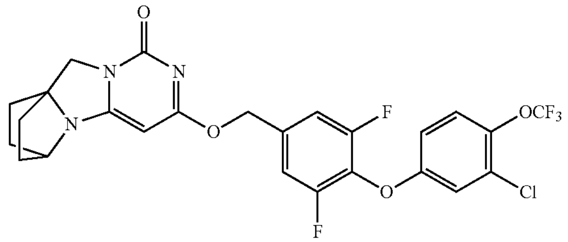

17

Step I: Preparation of Compound 17b

At room temperature, 3-chloro-4-(trifluoromethoxy) phenol 17a (0.50 g, 2.34 mmol), 3,4,5-trifluorobenzaldehyde 4a (0.41 g, 2.58 mmol) and potassium carbonate (0.42 g, 3.04 mmol) were dissolved in 20 mL of N,N-dimethylformamide, and stirred and reacted at 90° C. for 2 h. After cooled, the reactant was poured into 100 mL of ice water, and extracted with ethyl acetate (50 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a yellow solid product 17b (0.62 g, yield: 74.4%).

$^1$H NMR (400 MHz, $CDCl_3$) δ 9.94 (s, 1H), 7.63-7.54 (m, 2H), 7.29 (m, 1H), 7.07 (m, 1H), 6.90 (m, 1H).

Step II: Preparation of Compound 17c

At room temperature, 4-(3-chloro-4-(trifluoromethoxy) phenoxy)-3,5-difluorobenzaldehyde 17b (0.62 g, 1.94 mmol) was dissolved in 50 mL of methanol, to which $NaBH_4$ (62 mg, 1.94 mmol) was added at 0° C., stirred and reacted at room temperature for 0.5 h, concentrated under reduced pressure, added with water, and extracted with ethyl acetate (100 mL×2). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=4/1) by the silica gel column chromatography to give a colorless, oily product 17c (0.53 g, yield: 77.0%).

$^1$H NMR (400 MHz, $CDCl_3$) δ 7.25 (m, 1H), 7.06 (m, 2H), 7.01 (m, 1H), 6.87 (m, 1H), 4.72 (s, 2H), 2.04 (m, 1H).

Step III: Preparation of Compound 17

(4-(3-Chloro-4-(trifluoromethoxy) phenoxy)-3,5-difluorophenyl) methanol 17c (75 mg, 0.21 mmol) was dissolved in 5 mL of dry N,N-dimethylformamide, to which sodium hydride (60% in mineral oil, 17 mg, 0.42 mmol) was added at 0° C. After the materials were stirred and reacted at room temperature for 20 min, Compound 1g (50 mg, 0.21 mmol) was added, and stirred and reacted for 1 h. Thereafter, a small amount of water was added to quench the reaction.and purified with an eluent system (dichloromethane/methanol=20:1) by the silica gel column chromatography to give a white solid product 17 (23 mg, yield: 20%).

$^1$H NMR (400 MHz, $CDCl_3$) δ 7.23 (s, 1H), 7.09 (m, 2H), 7.03 (m, 1H), 6.87 (m, 1H), 5.39 (s, 2H), 5.21 (s, 1H), 4.13 (m, 1H), 4.01 (s, 2H), 2.10 (m, 2H), 1.83-1.71 (m, 6H). MS (ESI): m/z 555.9 $[M+H]^+$.

Example 18 Preparation of Compound 18

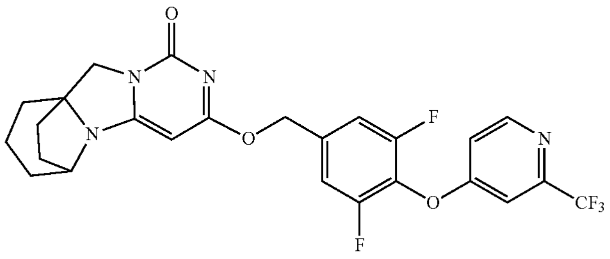

18

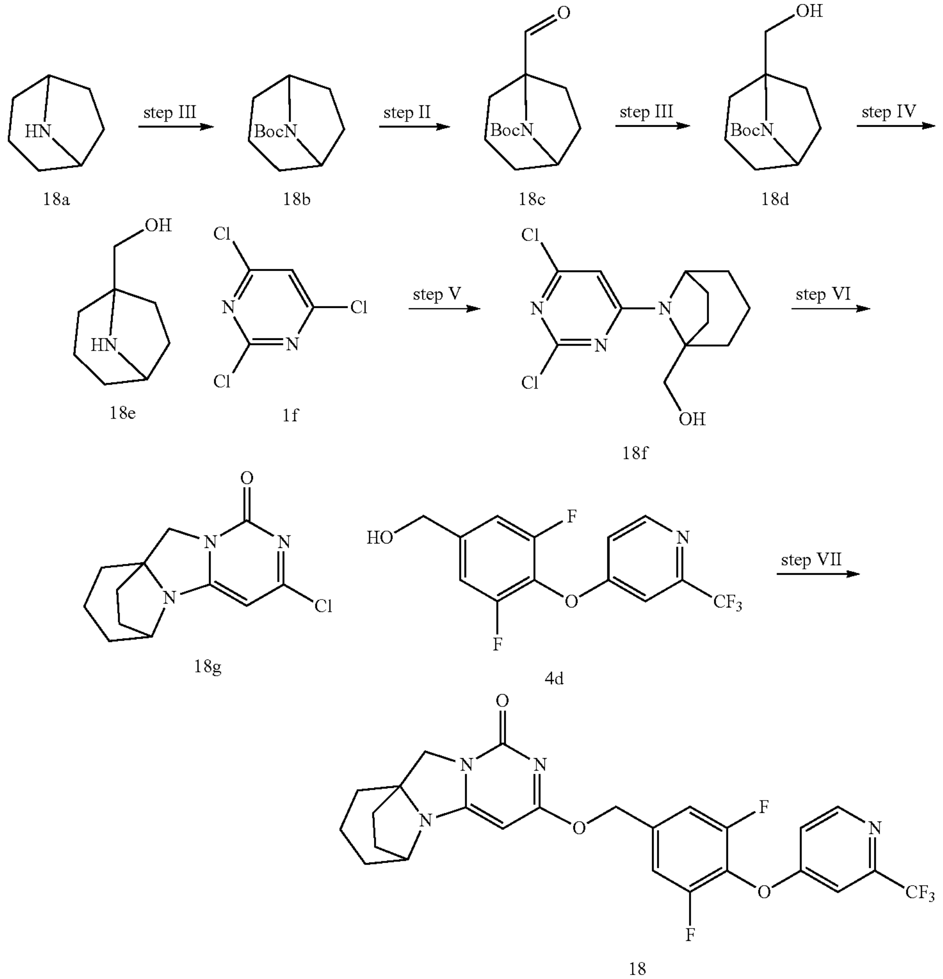

18a 18b 18c 18d 18e 1f 18f 18g 4d

18

Step I: Preparation of Compound 18b

At room temperature, 8-azabicyclo[3.2.1]octane 18a (5 g, 33.9 mmol) and triethylamine (5.2 g, 50.8 mmol) were dissolved in 300 mL of dichloromethane, and (Boc) 20 (11.1 g, 50.8 mmol) was added. The materials were stirred and reacted for 4 h, and extracted with dichloromethane (100 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a colorless liquid product 18b (9.4 g, 100%).

$^{1}$H NMR (400 MHz, $CDCl_3$) δ 4.14 (m, 2H), 1.97-1.86 (m, 2H), 1.81-1.53 (m, 6H), 1.46 (s, 9H), 1.41-1.35 (m, 2H).

Step II: Preparation of Compound 18c

At room temperature, tert-butyl 8-azabicyclo[3.2.1]octane-8-carboxylate 18b (7.2 g, 34.1 mmol) and TMEDA (4.7 g, 40.9 mmol) were dissolved in 150 mL of dry ether, and s-BuLi (1.3 M in hexane, 31.5 mL, 40.9 mmol) was added dropwise at −65° C. under nitrogen protection. After stirring and reacting at −65° C. for 30 min, a solution of methyl formate (2.45 g, 40.9 mmol) in ether (20 mL) was added dropwise. After stirring and reacting at −65° C. for 30 min, the reactant was heated to 0° C., stirred and reacted for 2 h, added with a saturated aqueous ammonium chloride solution (100 mL), and extracted with ether (50 mL×3). The organic phases were combined, dried over anhydrous sodium sulfate, and filtered to remove the drying agent. The filtrate was concentrated under reduced pressure, and purified with an eluent system (petroleum ether/ethyl acetate=10:1) by the silica gel column chromatography to give a colorless, liquid product 18c (3.13 g, 38.4%).

$^1$H NMR (400 MHz, $CDCl_3$) δ 9.45 (s, 1H), 4.24 (m, 1H), 2.15 (s, 1H), 1.97 (m, 1H), 1.85 (m, 2H), 1.82-1.60 (m, 6H), 1.45 (s, 9H).

Step III: Preparation of Compound 18d

At room temperature, tert-butyl 1-formyl-8-azabicyclo[3.2.1]octane-8-carboxylate 18c (3.13 g, 13.1 mmol) was dissolved in 100 mL of dry methanol, and $KBH_4$ (1.1 g, 19.6 mmol) was added in batch at 0° C. The materials were stirred and reacted at room temperature for 1 h, added with 40 mL of water, and extracted with dichloromethane (60 mL×3). The organic phases were combined, washed with saturated aqueous sodium chloride solution, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give a colorless liquid product 18d (3.45 g, 100%).

$^1$H NMR (400 MHz, $CDCl_3$) δ 5.37 (m, 1H), 4.21 (m, 1H), 3.72-3.49 (m, 2H), 2.00-1.73 (m, 4H), 1.61 (m, 6H), 1.46 (s, 9H).

Step IV: Preparation of Compound 18e

At room temperature, tert-butyl 1-(hydroxymethyl)-8-azabicyclo[3.2.1]octane-8-carboxylate 18d (3.13 g, 13.1 mmol) was dissolved in 60 mL of a mixed solvent of HCl/ethanol, stirred and reacted for 4 h, and concentrated under reduced pressure to give a yellow solid product 18e (2.45 g, 100%).

$^1$H NMR (400 MHz, DMSO) δ 8.94 (s, 2H), 5.55 (s, 1H), 3.80 (m, 1H), 3.58-3.48 (m, 2H), 2.04 (m, 1H), 1.86-1.40 (m, 9H).

Step V: Preparation of Compound 18f

At room temperature, (8-azabicyclo[3.2.1]oct-1-yl) methanol 18e (2.45 g, 17.35 mmol), 2,4,6-trichloropyrimidine (3.49 g, 19.1 mmol) and DIPEA (0.42 g, 52.05 mmol) were dissolved in 100 mL of acetonitrile, stirred and reacted overnight, concentrated under reduced pressure, and purified with an eluent system (petroleum ether/ethyl acetate=4:1) by the silica gel column chromatography to give a white solid product 18f (1 g, 20.1%).

$^1$H NMR (400 MHz, $CDCl_3$) § 6.41 (s, 1H), 5.43 (m, 1H), 4.30 (m, 1H), 3.83 (m, 1H), 3.72 (m, 1H), 2.13-1.52 (m, 10H).

Step VI: Preparation of Compound 18g 18f (1 g, 3.1 mmol) and triethylamine (0.94 g, 1.3 mmol) were dissolved in 50 mL of dry dichloromethane, and MsCl (0.4 g, 3.4 mmol) was added dropwise at 0° C. After stirring and reacting at 0° C. for 1 h, the reactant was concentrated under reduced pressure to give a colorless, oily intermediate (1.1 g, 100%). This coarse product and potassium carbonate (1.28 g, 9.3 mmol) were dissolved in 60 mL of a mixed solution of dioxane/water (1/1), stirred and reacted at 90° C. overnight, concentrated under reduced pressure, and purified with an eluent system (dichloromethane/methanol=20/1) by the silica gel column chromatography to give a white solid product 18g (0.4 g, 51%).

$^1$H NMR (400 MHz, $^1$H NMR (400 MHz, $CDCl_3$) δ 5.66 (s, 1H), 4.25 (m, 1H), 4.11 (m, 1H), 3.70 (m, 1H), 2.05-1.88 (m, 4H), 1.85-1.71 (m, 6H).

Step VII: Preparation of Compound 18

(3,5-Difluoro-4-((2-(trifluoromethyl)pyridin-4-yl)oxy) phenyl) methanol 4d (92 mg, 0.3 mmol) was dissolved in 5 mL of dry DMF, to which sodium hydride (60% in mineral oil, 17 mg, 0.4 mmol) was added at 0° C. After the materials were stirred and reacted at room temperature for 20 min, Compound 18g (50 mg, 0.2 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 18 (49 mg, yield: 47%).

$^1$H NMR (400 MHz, $CDCl_3$) δ 8.60 (m, 1H), 7.26 (s, 1H), 7.13 (m, 2H), 6.98 (m, 1H), 5.41 (s, 2H), 5.19 (s, 1H), 4.24 (m, 1H), 4.07 (m, 1H), 3.70 (m, 1H), 2.05-1.87 (m, 3H), 1.73 (m, 7H). MS (ESI): m/z 521.2 [M+H]$^+$.

Example 19 Preparation of Compound 19

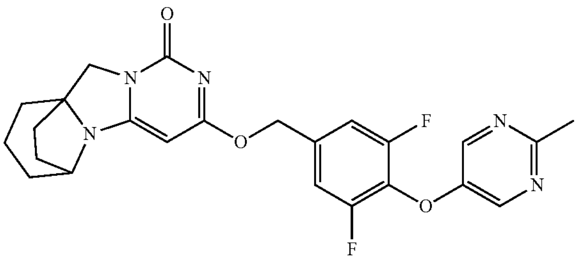

19

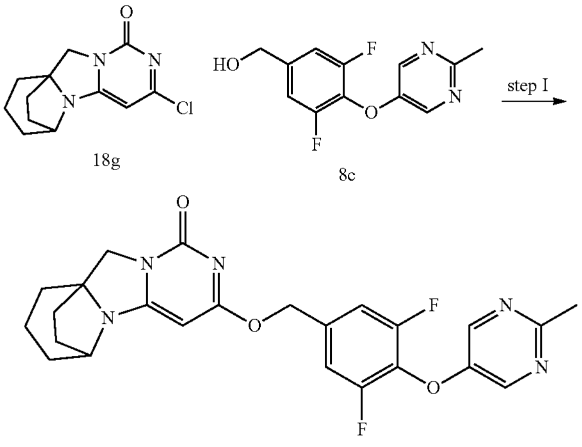

18g

8c

19

Step I: Preparation of Compound 19

(3,5-Difluoro-4-((2-methylpyridin-4-yl)oxy)phenyl) methanol 8c (53 mg, 0.21 mmol) was dissolved in 5 mL of dry DMF, to which sodium hydride (60% in mineral oil, 17 mg, 0.4 mmol) was added at 0° C. After the materials were stirred and reacted at room temperature for 20 min, Compound 18g (50 mg, 0.2 mmol) was added, and stirred and reacted for 1 h. Thereafter, a small amount of water was added to quench the reaction. The reactant was purified with an eluent system (dichloromethane/methanol=20:1) by the silica gel column chromatography to give a white solid product 19 (52 mg, yield: 55.5%).

$^1$H NMR (400 MHz, $CDCl_3$) δ 8.38 (s, 2H); 7.10 (m, 2H), 5.41 (s, 2H), 5.20 (s, 1H), 4.23 (m, 1H), 4.06 (m, 1H), 3.68 (m, 1H), 2.70 (s, 3H), 2.00-1.90 (m, 3H), 1.85-1.69 (m, 7H). MS (ESI): m/z 468.2 [M+H]$^+$.

Example 20 Preparation of Compound 20

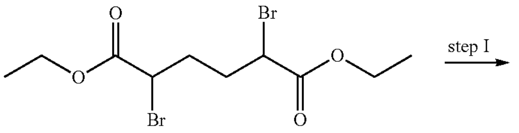

20a

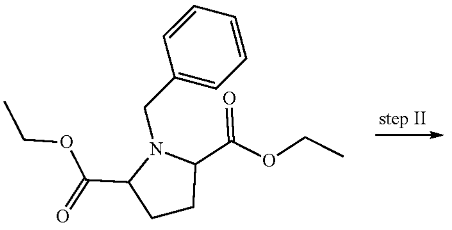

20b

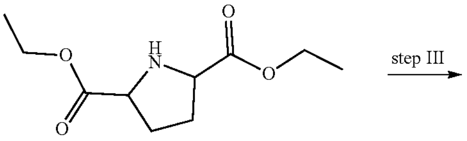

20c

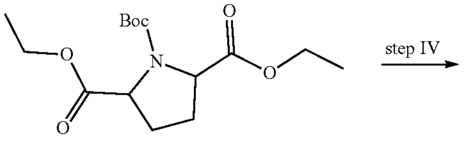

20d

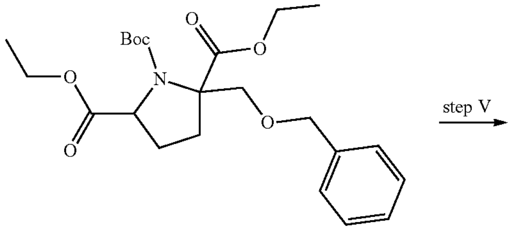

20e

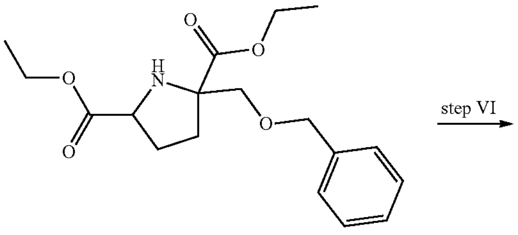

20f

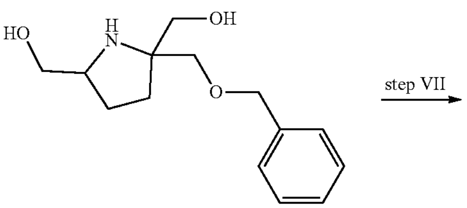

20g

-continued

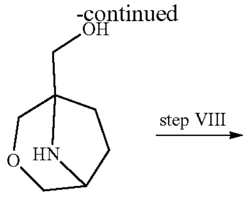

20h

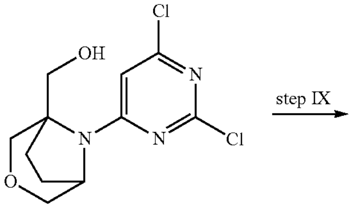

20i

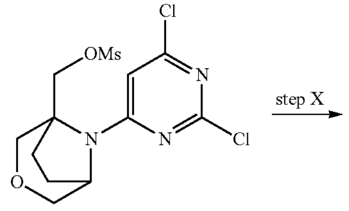

20j

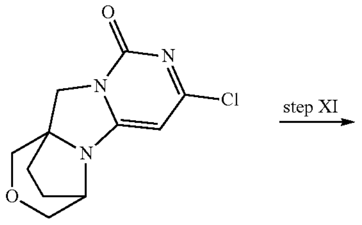

20k

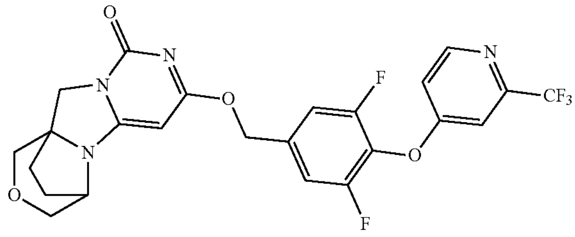

20

Step I: Preparation of Compound 20b

At room temperature, the compound diethyl meso-2,5-dibromoadipate (10.0 g; 27.8 mmol) and potassium carbonate (4.60 g, 33.3 mmol) were dissolved in toluene and water (200 mL, v/v=4:1), and phenylmethylamine (2.99 g, 27.8 mmol) was added. The reaction mixture was heated to 80° C. and reacted for 24 h. The reaction mixture was cooled to room temperature, concentrated under reduced pressure to remove most of the solvent, added with water, and extracted with ethyl acetate (80 mL×3). The organic layers were combined, dried over anhydrous sodium sulfate, and filtered to remove the drying agent. The filtrate was concentrated under reduced pressure, and purified with an eluent system (petroleum ether/ethyl acetate=10/1) by the silica gel column chromatography to give an oily product 20b (6.6 g, 77.7%).

$^1H$ NMR (400 MHz, DMSO) δ 7.31-7.18 (m, 5H), 3.96-3.86 (m, 4H), 3.83 (s, 2H), 3.38 (m, 2H), 2.08-1.98 (m, 2H), 1.94-1.83 (m, 2H), 1.08 (m, 6H).

Step II: Preparation of Compound 20c

At room temperature, the compound diethyl N-benzyl-2,5-pyrrole dicarboxylate (6.6 g, 21.6 mmol) was dissolved in methanol (100 mL), and palladium on carbon (20%, 1.3 g) was added. The reaction mixture was reacted for 7 h at room temperature under the $H_2$ condition. The reaction mixture was filtered, and the filtrate was concentrated under reduced pressure to give a colorless, oily Compound 20c (4.4 g, 94.4%).

$^1$H NMR (400 MHz, $CDCl_3$) δ 4.23-4.11 (m, 4H), 3.81-3.71 (m, 2H), 2.18-2.06 (m, 2H), 1.97-1.83 (m, 2H), 1.26 (m, 6H).

Step III: Preparation of Compound 20d

At room temperature, the compound diethyl 2,5-pyrrolidinecarboxylate (4.4 g, 19.5 mmol) was dissolved in toluene, and di-tert-butyl dicarbonate (5.35 g, 24.5 mmol) was added. The reaction mixture was heated to 95° C. and reacted for 4 h. The reaction mixture was cooled to room temperature, concentrated under reduced pressure, and purified with an eluent system (petroleum ether/ethyl acetate=5/1) by the silica gel column chromatography to give a colorless, oily product 20d (4.3 g, 70.0%).

$^1$H NMR (400 MHz, $CDCl_3$) δ 4.38 (s, 1H), 4.27 (s, 1H), 4.24-4.14 (m, 4H), 2.16 (m, 4H), 1.42 (s, 9H), 1.31-1.21 (m, 6H).

Step IV: Preparation of Compound 20e

At room temperature, the compound diethyl N-tert-butoxycarbonyl-2,5-pyrrole dicarboxylate (2.7 g, 8.6 mmol) was dissolved in dry tetrahydrofuran (80 mL). A solution of lithium diisopropylamide (2 M, 8.2 ml, 16.3 mmol) in tetrahydrofuran was added dropwise at −78° C. under nitrogen protection. Benzylchloromethyl ether (1.49 g, 9.5 mmol) was added. The mixture was stirred and reacted at −78° C. for 1 h, and heated to the room temperature and reacted for 2 h. To the reaction mixture, 100 mL of saturated aqueous ammonium chloride solution was added, and extracted with ethyl acetate (50 mL×3). The organic phases were combined, dried over anhydrous sodium sulfate, and filtered to remove the drying agent. The filtrate was concentrated under reduced pressure, and purified with an eluent system (petroleum ether/ethyl acetate=5/1) by the silica gel column chromatography to give a yellow, oily product 20e (2.3 g, 61.4%).

$^1$H NMR (400 MHz, $CDCl_3$) δ 7.41-7.20 (m, 5H), 4.71-4.52 (m, 2H), 4.25-4.07 (m, 4H), 2.49 (m, 1H), 2.28 (m, 1H), 2.15-2.01 (m, 2H), 1.37 (s, 9H), 1.29-1.17 (m, 6H).

Step V: Preparation of Compound 20f

At room temperature, the compound diethyl N-tert-butoxycarbonyl-2,5-(2-phenoxymethyl) pyrrole dicarboxylate was dissolved in dioxane hydrochloride (4N, 20 mL), and stirred at room temperature for 2 h. The reaction mixture was concentrated under reduced pressure to give a brown oily coarse Compound 20f (1.44 g, 50.0%) for direct use in the next step without purification.

$^1$H NMR (400 MHz, $CDCl_3$) δ 7.39-7.27 (m, 5H), 4.60-4.46 (m, 2H), 3.71 (m, 1H), 3.55 (m, 2H), 3.44-3.27 (m, 3H), 1.89-1.76 (m, 1H), 1.76-1.45 (m, 3H).

Step VI: Preparation of Compound 20g

Dry tetrahydrofuran (40 mL) was added to a reaction flask, and lithium aluminum hydride (0.33 g, 8.6 mmol) was added under ice bath and nitrogen protection. Ten minutes later, a solution of [6-(benzyloxymethyl)-6-(hydroxymethyl)-2-piperidinyl]methanol in tetrahydrofuran was added dropwise, and then moved to room temperature and reacted for 1 h. The reaction was performed under ice-bath conditions again, and sodium hydroxide solution (2M, 2 mL) was added to produce a white solid. The white solid was filtered and washed with tetrahydrofuran. The filtrate was dried over anhydrous sodium sulfate, and filtered to remove the drying agent. The filtrate was concentrated under reduced pressure to give a yellowish oily coarse Compound 20g (1.0 g, 92.5%) for direct use in the next step without purification.

$^1$H NMR (400 MHz, $CDCl_3$) δ 7.39-7.27 (m, 5H), 4.57-4.46 (m, 2H), 3.71 (m, 1H), 3.55 (m, 2H), 3.44-3.31 (m, 3H), 1.88-1.78 (m, 1H), 1.75-1.58 (m, 2H), 1.52 (m, 1H).

Step VII: Preparation of Compound 20h

At room temperature, the compound (2-((benzyloxy) methyl) pyrrolidine-2,5-diyl)dimethanol (1.0 g, 3.98 mmol) was dissolved in methanesulfonic acid under argon protection. The reaction mixture was heated to 140° C. and reacted for 8 h. After cooling to room temperature, the reaction solution was poured into ice water (20 ml), 24 ml of 50% sodium hydroxide was added at 0° C. After concentrated under reduced pressure, the mixture was dissolved in methanol and filtered, and the filtrate was concentrated under reduced pressure to give a yellowish oily coarse target Compound 20h (0.3 g, 52.8%).

Step VIII: Preparation of Compound 20i

At room temperature, the compound 3-oxa-8-azabicyclo [3.2.1]oct-5-ylmethanol (0.3 g, 2.1 mmol), 2,4,6-trichloropyrimidine (0.46 g, 2.5 mmol), and diisopropylethylamine (0.81 g, 6.3 mmol) were dissolved in acetonitrile (20 ml), and the reaction mixture was stirred at room temperature overnight. The reaction mixture was concentrated under reduced pressure, and purified with an eluent system (petroleum ether/ethyl acetate=2:1) by the silica gel column chromatography to give a white solid compound 20i (0.15 g, 24.8%).

$^1$H NMR (400 MHz, $CDCl_3$) δ 6.39 (s, 1H), 5.25 (m, 1H), 4.22 (m, 1H), 3.98-3.76 (m, 3H), 3.67 (m, 3H), 2.23-2.14 (m, 1H), 2.14-1.96 (m, 2H), 1.78 (m, 1H).

Steps IX & X: Preparation of Compound 20k

At room temperature, the compound (8-(2,6-dichloropyrimidin-4-yl)-3-oxa-8-azabicyclo[3.2.1]oct-1-yl) methanol (0.15, 24.8%) was dissolved in dry dichloromethane, triethylamine (158 mg, 1.56 mmol) was added, and placed in an ice bath. Methanesulfonyl chloride (66 mg, 0.57 mmol) was slowly added. The reaction mixture was reacted in the ice bath for 1 h. The reaction mixture was concentrated under reduced pressure to give a white solid compound, which was used directly in the next step without purification. The coarse product and potassium carbonate (215 mg, 1.56 mmol) were dissolved in dioxane and water (40 mL, 1/1). The reaction mixture was reacted at room temperature overnight. The reaction mixture was concentrated under reduced pressure, and purified with an eluent system (dichloromethane/methanol=20/1) by the silica gel column chromatography to give a white solid Compound 20k (40 mg, 30.8%).

$^1$H NMR (400 MHz, $CDCl_3$) δ 5.72 (s, 1H), 4.29 (m, 1H), 4.08 (m, 1H), 3.97 (m, 1H), 3.77 (m, 4H), 2.46-2.27 (m, 1H), 2.14 (m, 1H), 1.96 (m, 1H), 1.77 (m, 1H).

Step XI: Preparation of Compound 20

At room temperature, the compound (3,5-difluoro-4-((2-(trifluoromethyl)pyridin-4-yl)oxy)phenyl) methanol (58, 0.19 mmol) was dissolved in dry N,N-dimethylformamide (5 mL), and sodium hydride (60% in mineral oil, 13 mg, 0.32 mmol) was added in an ice bath. 7-Chloro-3,4-dihydro-1H-4,11a-ethanopyrimido[6',1': 2,3]imidazo[5,1-c][1,4]azinyl-9 (11H)-one (40 mg, 0.16 mol) was added 15 min later, and reacted at room temperature for 1 h. The reaction mixture was quenched by adding ice water, and extracted with ethyl acetate (20 ml×3). The organic layers were combined, dried over anhydrous sodium sulfate, and filtered to remove the drying agent. The filtrate was concentrated under reduced pressure, and purified with an eluent system (dichloromethane/methanol=20/1) by the silica gel column chromatography to give a white solid compound 20 (35 mg, 35.3%).

$^1$H NMR (600 MHz, $CDCl_3$) δ 8.61 (m, 1H), 7.26 (s, 1H), 7.14 (m, 2H), 6.99 (m, 1H), 5.43 (s, 2H), 5.22 (s, 1H), 4.26 (m, 1H), 4.00 (m, 1H), 3.93 (m, 1H), 3.78-3.68 (m, 4H), 2.33-2.26 (m, 1H), 2.08 (m, 1H), 1.99-1.92 (m, 1H), 1.73 (m, 1H). m/z 523.0 $[M+H]^+$.

Biological Evaluation

The bioactivity of a compound could be determined using any suitable assay as well as tissue and in vivo model for determining the activity of a compound as an LpPLA2 inhibitor.

(1) Recombinant Human Lp-PLA2 Assay (rhLp-PLA2), Also Referred to as PED6 Assay

PED6 was a fluorescently-labeled phospholipid that could be purchased dorectly from Invitogene or Molecular Probes. It had a fluorescence-quenching p-nitrophenyl group at the Sn3 position and a Bodipy fluorescein (FL) group at the sn2 position. Once cleaved by the Lp-PLA2 enzyme, it would release the FL group, resulting in enhanced fluorescence. However, the Lp-PLA2 inhibitor could prevent occurrence of such cleavage, so that no enhanced fluorescence could be observed.

Assay Method: The compound to be tested (as shown in Table 1) was mixed with a DMSO solution in a volume ratio of 1:3, and diluted to prepare a source plate of a 384-well microplate. Then 0.01 μl of the compound was transferred via an ECHO liquid dispenser from the source plate to a 384-well Greiner 784076 plate, and 5 μl of a buffer consisting of 50 mM HEPES, pH7.4, 150 mM NaCl, and 1 mM CHAPS (the buffer solution containing a recombinant human Lp-PLA2 enzyme at a concentration of 4 nM or 110 μM) was added to each well of the plate. The plate was centrifuged at 500 rpm for 10 seconds. After a 30-min pre-incubation, 5 μl of the above-mentioned buffer was added to a 384-well Greiner 784076 plate, the plate was centrifuged at 500 rpm for 10 seconds. After the plate was incubated at room temperature for 20 min in a dark place, the fluorescence intensity was read at ex 480/em 540 with a ViewLux microplate imager, and the XL fitting model in Excel was used to perform the curve analysis and QC analysis to calculate pIC50. The results were listed in Table 1.

TABLE 1

| Compound No. | rhLp-PLA2 ($pIC_{50}$) |
|---|---|
| 1 | 8.6 |
| 2 | 9.1 |
| 3 | 9.3 |
| 4 | 10.4 |
| 5 | 10.5 |
| 6 | 10.3 |
| 7 | 10.4 |
| 8 | 10.5 |
| 9 | 10.0 |
| 10 | 10.2 |
| 11 | 10.1 |
| 12 | 10.1 |
| 13 | 9.6 |
| 14 | 10.1 |
| 16 | 10.0 |
| 17 | 10.1 |

TABLE 1-continued

| Compound No. | rhLp-PLA2 ($pIC_{50}$) |
|---|---|
| 18 | 10.0 |
| 19 | 9.5 |
| Positive compound Rilapladib | 8.9 |

(2) Assay of Lp-PLA2 in Human Plasma (Also Referred to as Thio-PAF Assay)

The human plasma assay was conducted using the sulphatide analog of PAF (phosphatidylcholine). After hydrolysis, it would generate phospholipids containing free sulfhydryl groups, which would be subjected to Michael addition with CPM to generate fluorescence-enhancing maleimide. Continuous quantitative analysis of thiol could be conducted by detecting the fluorescence intensity. This assay could be used to detect the inhibitory activity of the Lp-PLA2 inhibitor on the Lp-PLA2 enzyme in human plasma.

Assay Method: The compound to be tested (as shown in Table 2) was mixed with a DMSO solution in a volume ratio of (1:3), and diluted to prepare a source plate of a 384-well microplate. Then 0.01 μl of the compound was transferred via an ECHO liquid dispenser from the source plate to a 384-well Greiner 784076 plate, and 8 μl of pre-aliquoted and frozen mixed human plasma was then added. The plate was centrifuged at 500 rpm for 10 seconds. After a 30-min pre-incubation, 2 μl of a substrate solution, and a buffer containing 2.5 mM 2-thio-PAF (a solution in ethanol), 32 μM CPM (a solution in DMSO) and 3.2 mM N-ethylmaleimide (NEM) (a buffer solution consisting of 50 mM HEPES, pH7.4, 150 mM NaCl, 1 mM CHAPS) was added by a BRAVO liquid handling station to a 384-well Greiner 784076 low-volume plate. Two minutes later, the reaction was quenched with 5 μl of 5% trifluoroacetic acid. After the plate was incubated at room temperature for 40 min in a dark place, the fluorescence intensity was read at ex 380/em 485 with an Envision microplate reader, and the XL fitting model in Excel was used to perform the curve analysis and QC analysis to calculate pIC50. The results were listed in Table 2.

TABLE 2

| Compound No. | Thio-PAF ($pIC_{50}$) |
|---|---|
| 1 | 7.0 |
| 2 | 7.6 |
| 3 | 7.8 |
| 4 | 8.4 |
| 5 | 8.2 |
| 6 | 8.1 |
| 7 | 8.5 |
| 8 | 8.1 |
| 9 | 7.9 |
| 10 | 8.1 |
| 11 | 7.9 |
| 12 | 8.0 |
| 13 | 7.7 |
| 14 | 8.1 |
| 16 | 7.9 |
| 17 | 8.0 |
| 18 | 8.1 |
| 19 | 7.8 |
| Positive compound Rilapladib | 7.8 |

The invention claimed is:

1. A compound represented by formula (I):

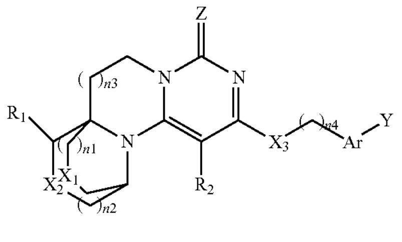

or a pharmaceutically acceptable salt thereof, wherein:

$n_1$, $n_2$, $n_3$, and $n_4$ are each independently 0, 1, or 2;

$R^1$ and $R^2$ are each independently selected from: —H, hydroxyl, cyano, halogen, alkyl, deuteroalkyl, hydroxyalkyl, haloalkyl, cycloalkyl, and alkoxyl;

$X_1$, $X_2$, and $X_3$ are each independently selected from: alkylene, —O—, —S—, or —NR'—;

R' is selected from: —H, alkyl, deuteroalkyl, or cycloalkyl;

Ar is an unsubstituted or substituted arylene or heteroarylene; wherein, in the substituted arylene or heteroarylene, one or more hydrogen atoms are replaced by one or more substituents that are each independently selected from: halogen, alkyl, haloalkyl, alkoxyl, haloalkoxyl, deuteroalkyl, deuteroalkoxyl, hydroxyl, hydroxyalkyl, cyano, amino, monoalkyl- or dialkyl-substituted amino, nitro, carboxyl, aldehyde, cycloalkyl, heterocyclyl, aryl, or heteroaryl;

Y is —H, halogen, alkyl, haloalkyl, haloalkoxyl, cycloalkyl, alkoxyl, deuteroalkyl, deuteroalkoxyl, —OAr', —SAr', —NH—Ar', —NMe—Ar', —NR'R", or —R'"—Ar';

Ar' is an unsubstituted or substituted aryl or heteroaryl; wherein, in the substituted aryl or heteroaryl, one or more hydrogen atoms are replaced by one or more substituents that are each independently selected from: halogen, alkyl, haloalkyl, alkoxyl, hydroxyl, hydroxyalkyl, haloalkoxyl, deuteroalkyl, deuteroalkoxyl, cyano, amino, nitro, carboxyl, aldehyde, cycloalkyl, heterocyclyl, aryl, or heteroaryl;

R" is alkyl;

R'" is alkylene; and

Z is O or S.

2. The compound of formula (I), or the pharmaceutically acceptable salt thereof according to claim 1, wherein halogen atoms in the "halogen", "haloalkyl", and "haloalkoxyl" are each independently selected from F, Cl, Br, or I;

alkyls in the "alkyl", "deuteroalkyl", "deuteroalkoxyl", "hydroxyalkyl", "haloalkyl", "haloalkoxyl", "alkoxyl", and "monoalkyl- or dialkyl-substituted amino" are each independently $C_1$-$C_{10}$ linear or branched alkyl;

"alkylene" is $C_1$-$C_{10}$ linear or branched alkylene;

"cycloalkyl" is $C_3$-$C_{10}$ monocyclic or bicyclic cycloalkyl;

"heterocyclyl" is 3- to 10-membered non-aromatic heterocyclic ring containing 1, 2, or 3 heteroatoms selected from N, O, and S on the ring;

"aryl" is 6- to 10-membered aryl, phenyl or naphthyl, and optionally phenyl, 1-naphthyl, or 2 naphthyl;

"arylene" is 6- to 10-membered arylene, and phenylene or naphthylene;

"heteroaryl" is a 5- to 10-membered heteroaromatic ring containing 1 to 3 heteroatoms selected from N, O, and S on the ring; and "heteroarylene" is a 5- to 10-membered heteroarylene ring containing 1 to 3 heteroatoms selected from N, O, and S on the ring.

3. The compound of formula (I), or the pharmaceutically acceptable salt thereof according to claim 1, wherein $n_1$, $n_2$, $n_3$, and $n_4$ are each independently 0, 1, or 2;

$R_1$ and $R_2$ are each independently selected from: —H, F, Cl, Br, hydroxyl, cyano, $C_1$-$C_7$ alkyl, $C_1$-$C_3$ deuteroalkyl, cyclopropanyl, cyclobutanyl, or cyclopentyl;

$X_1$, $X_2$, and $X_3$ are each independently selected from: $C_1$-$C_7$ alkylene, —O—, —S—, or —NR'—;

R' is selected from-H, $C_1$-$C_7$ alkyl, deuteroalkyl, or $C_3$-$C_6$ cycloalkyl;

Ar is phenylene or pyridyl, and a hydrogen atom in the phenylene or pyridyl is substituted by 1, 2, or 3 substituents that are each independently selected from: F, Cl, Br, I, —CN, —Me, —$C_2H_5$, cyclopropyl, —$CD_3$, —OMe, or —$OCF_3$;

Y is —H, —F, —Cl, —Br, methyl, ethyl, n-propyl, isoproyl, —$CD_3$, —$CF_3$, —$CH_2CF_3$, —$OCF_3$, —$OCHF_2$, cyclopropyl, -cyclobutyl, -cyclopentyl, —$OCH_3$, —$OC_2H_5$, —$OC_3H_7$, or —OAr';

Ar' is an unsubstituted or substituted phenyl, pyridyl, pyrimidinyl, or quinolinyl, wherein, in the substituted phenyl, pyridyl, pyrimidinyl, or quinolinyl, one, two, or three hydrogen atoms in the phenyl, pyridyl, pyrimidinyl or quinolinyl ring are each independently replaced with 1, 2 or 3 substituents that are each independently selected from: F, Cl, Br, —CN, $C_1$-$C_7$ alkyl, —$CD_3$, $C_1$-$C_6$ haloalkyl, —$OCH_3$, —$OC_2H_7$, —$OC_3H_7$, $C_1$-$C_6$ haloalkoxyl, or $C_3$-$C_6$ cycloalkyl; and Z is O.

4. The compound of formula (I), or the pharmaceutically acceptable salt thereof according to claim 1, wherein the compound of formula (I) is selected from the following compounds:

1

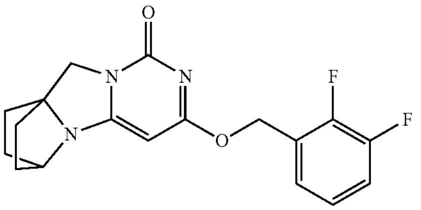

2

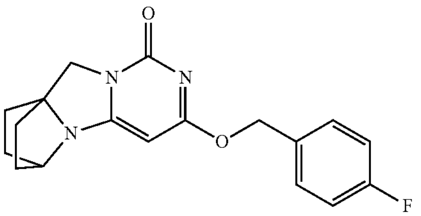

3

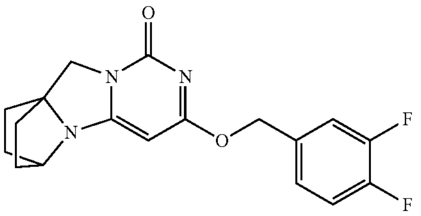

-continued
4
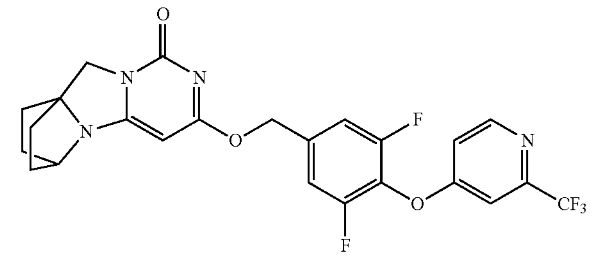
5
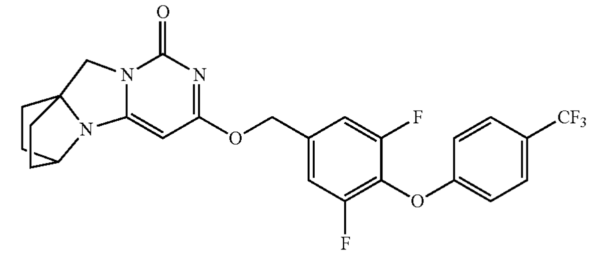
6
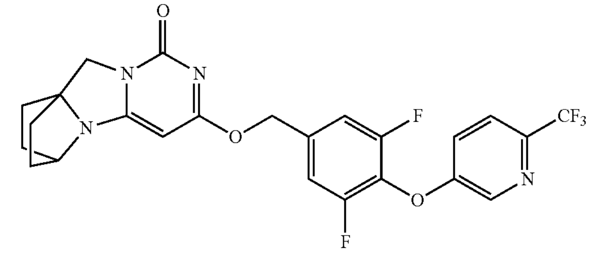
7
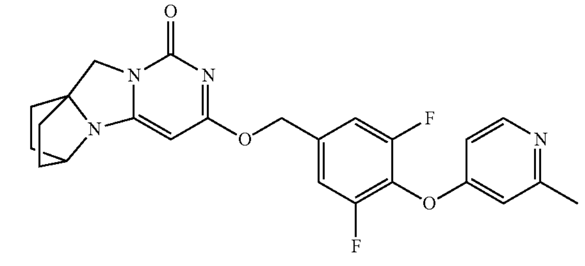
8
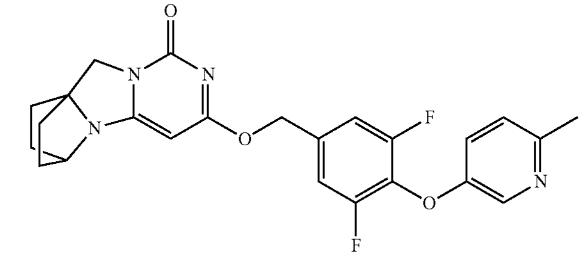
-continued
9
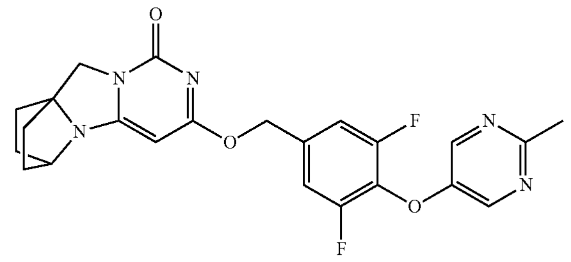
10
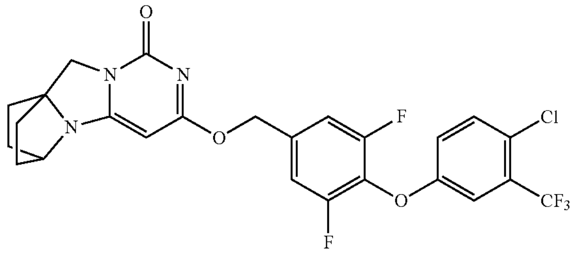
11
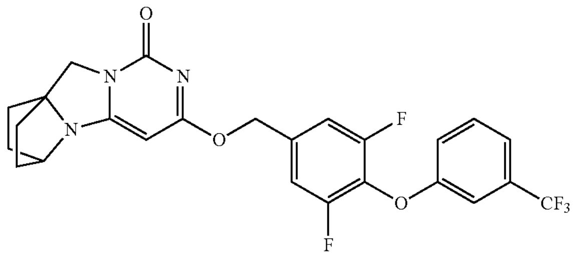
12
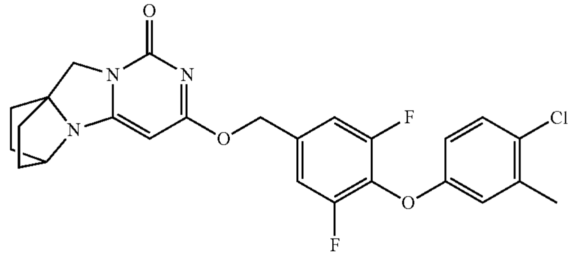
13
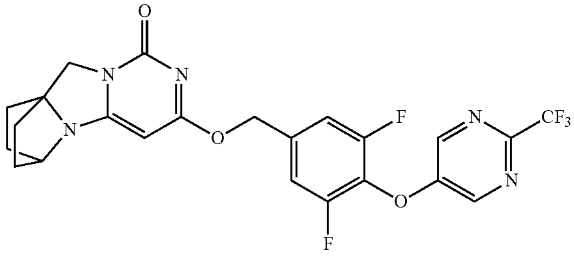

-continued

14

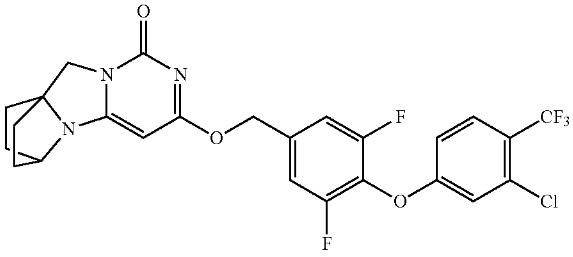

15

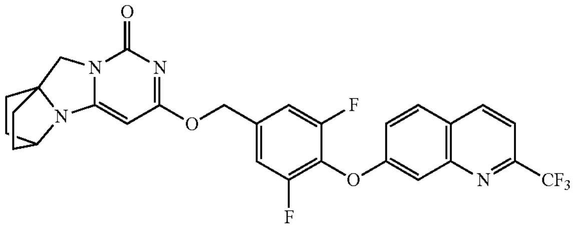

16

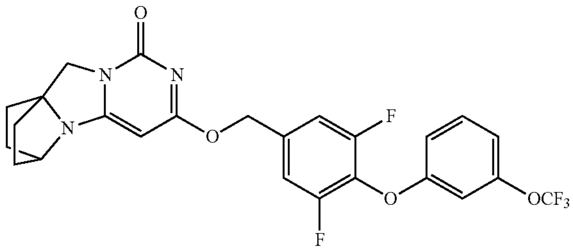

17

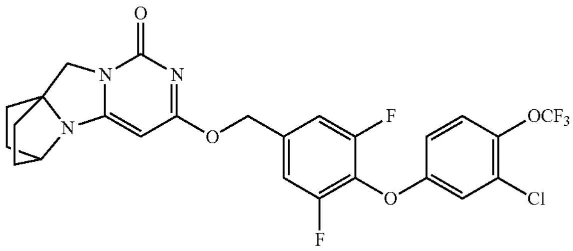

18

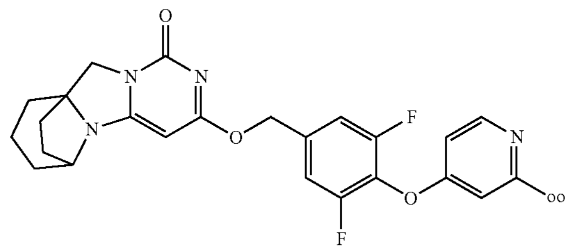

19

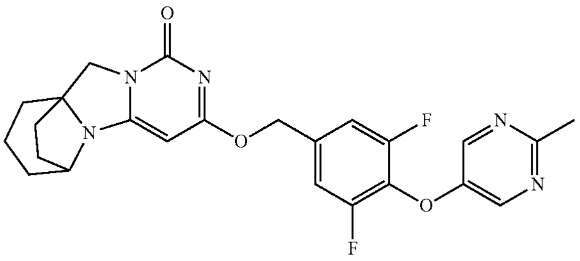

-continued

20

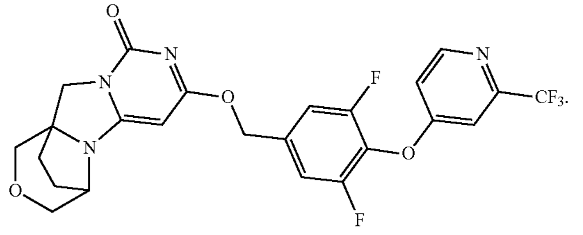

5. The compound of formula (I), or the pharmaceutically acceptable salt thereof according to claim 1, wherein the pharmaceutically acceptable salt is selected from the group consisting of an alkali metal salt, an alkaline earth metal salt, and an ammonium salt of the compound of formula (I); and the alkali metal is selected from the group consisting of sodium, potassium, lithium, and cesium, and the alkaline earth metal is selected from the group consisting of magnesium, calcium, and strontium.

6. A method for preparing a compound of formula (I), or a pharmaceutically acceptable salt thereof according to claim 1, comprising the following synthetic route:

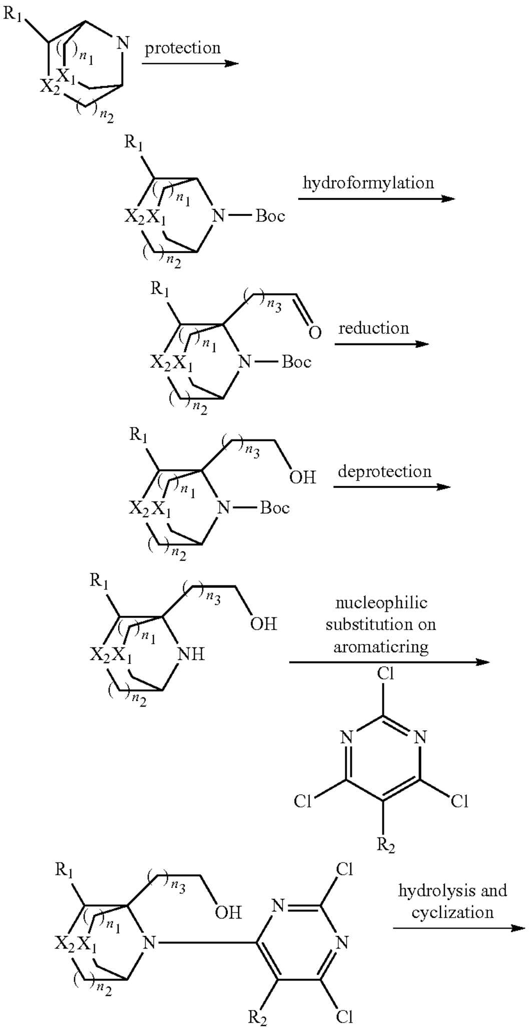

-continued

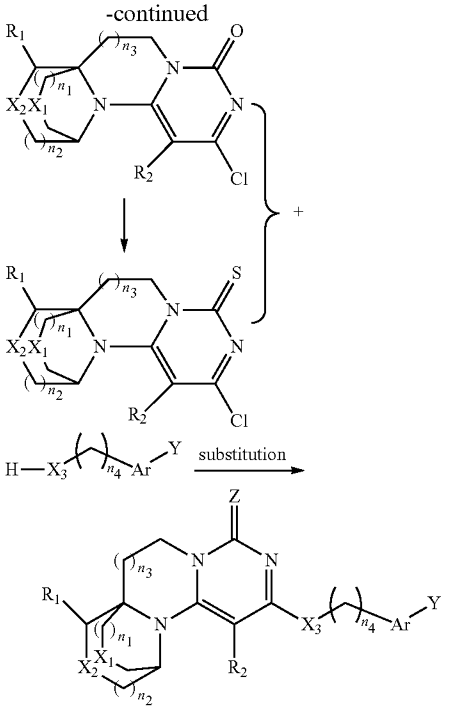

in respective formulas, $n_1$, $n_2$, $n_3$, $R_1$, $R_2$, $X_1$, $X_2$, $X_3$, Z, Ar, and Y are as defined.

7. A pharmaceutical composition, comprising one or more of a compound of formula (I), or a pharmaceutically acceptable salt thereof according to claim 1, and a pharmaceutically acceptable carrier.

8. The pharmaceutical composition according to claim 7, wherein a dosage form of the pharmaceutical composition is selected from the group consisting of an oral preparation, a rectally administered preparation, and a parenteral administered preparation;

the oral preparation is selected from the group consisting of a solid preparation and a liquid preparation, the solid preparation is selected from the group consisting of tablets, powders, granules, and capsules;

the liquid preparation is selected from the group consisting of aqueous or oily suspensions, and syrups; and the parenteral administered preparation is selected from the group consisting of solutions for injection, and aqueous or oily suspensions.

9. The pharmaceutical composition according to claim 7, wherein the pharmaceutical composition is for use in preparing an Lp-PLA2 inhibitor.

10. The pharmaceutical composition according to claim 7, wherein the pharmaceutical composition is for use in preparing a medicament for treating a neurodegenerative-related disease, wherein the neurodegenerative-related disease is selected from the group consisting of Alzheimer's disease, glaucoma, and age-related macular degeneration.

11. The pharmaceutical composition according to claim 7, wherein the pharmaceutical composition is for use in preparing a medicament for treating cardiovascular disease, diabetic macular edema, or prostatic disease.

12. The compound of formula (I), or the pharmaceutically acceptable salt thereof according to claim 1, wherein the pharmaceutically acceptable salt is a salt formed with an organic base selected from the group consisting of trialkylamine, pyridine, quinoline, piperidine, imidazole, picoline, dimethylaminopyridine, dimethylaniline, N-alkylmorpholine, 1,5-diazabicyclo[4.3.0]nonene-5, 1,8-diazabicyclo[5.4.0]undecene-7, and 1,4-diazabicyclo[2.2.2]octane, the trialkylamine is selected from the group consisting of trimethylamine, triethylamine, and N-ethyldiisopropylamine, and the N-alkylmorpholine is N-methylmorpholine.

13. The compound of formula (I), or the pharmaceutically acceptable salt thereof according to claim 1, wherein the pharmaceutically acceptable salt is a salt formed with an acid selected from the group consisting of hydrochloric acid, hydrobromic acid, hydroiodic acid, sulfuric acid, nitric acid, phosphoric acid, carbonic acid, formic acid, acetic acid, propionic acid, oxalic acid, malonic acid, succinic acid, fumaric acid, maleic acid, lactic acid, malic acid, citric acid, tartaric acid, picric acid, methanesulfonic acid, ethanesulfonic acid, p-toluenesulfonic acid, glutamic acid, and pamoic acid.

14. A method of treating a neurodegenerative-related disease in a subject in need thereof, comprising administering to the subject a compound of Formula (I) or a pharmaceutically acceptable salt thereof according to claim 1, wherein the neurodegenerative-related disease is selected from the group consisting of Alzheimer's disease, glaucoma, and age-related macular degeneration.

15. A method of treating atherosclerosis, diabetic macular edema, or a prostate cancer in a subject in need thereof, comprising administering to the subject a compound of formula (I) or a pharmaceutically acceptable salt thereof according to claim 1.

* * * * *